United States Patent
Horibe et al.

(10) Patent No.: US 6,583,164 B1
(45) Date of Patent: Jun. 24, 2003

(54) ANTIMYCOTIC DRUG COMPOSITION

(75) Inventors: Hidetoshi Horibe, Toyonaka (JP); Yoko Nishida, Ibaraki (JP); Masao Nagao, Itami (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/787,656

(22) PCT Filed: Sep. 28, 1999

(86) PCT No.: PCT/JP99/05292

§ 371 (c)(1),
(2), (4) Date: Mar. 19, 2001

(87) PCT Pub. No.: WO00/18401

PCT Pub. Date: Apr. 6, 2000

(30) Foreign Application Priority Data

Sep. 29, 1998 (JP) ............................................. 10-275570

(51) Int. Cl.$^7$ ......................... A61K 31/41; A61K 31/70; C07D 403/14

(52) U.S. Cl. ............................ 514/381; 514/23; 514/53; 548/253

(58) Field of Search ............................ 514/23, 53, 381; 548/523

(56) References Cited

U.S. PATENT DOCUMENTS

| | | |
|---|---|---|
| 4,814,332 A | 3/1989 | Klötzer et al. |
| 4,831,151 A | 5/1989 | Link et al. |
| 5,371,100 A | 12/1994 | Itoh et al. |
| 5,371,101 A | 12/1994 | Itoh et al. |
| 5,495,024 A | 2/1996 | Itoh et al. |
| 5,545,652 A | 8/1996 | Itoh et al. |
| 5,792,780 A | 8/1998 | Itoh et al. |
| 5,888,531 A | 3/1999 | Ohshika et al. |
| 6,034,248 A | 3/2000 | Itoh et al. |
| 6,407,129 B1 * | 6/2002 | Itoh et al. ................... 514/381 |

FOREIGN PATENT DOCUMENTS

| | | |
|---|---|---|
| JP | 9-124481 | 5/1997 |
| WO | WO 98/43970 | 10/1998 |

* cited by examiner

*Primary Examiner*—Elli Peselev
(74) *Attorney, Agent, or Firm*—Mark Chao; Elaine M. Ramesh

(57) ABSTRACT

The composition of the present invention comprises a quaternized nitrogen-containing imidazole-1-yl or 1,2,4-triazole-1-yl compound wherein one of the nitrogen atoms constituting the azole ring is quaternized with a group eliminating in vivo and represented by the formula:

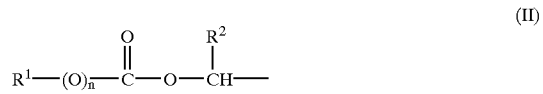

(II)

wherein $R^1$ represents a hydrocarbon or heterocyclic group which may be substituted, $R^2$ represents a hydrogen atom or a lower alkyl group, and n is 0 or 1, and a saccharide, said compound being capable of being converted into an antifungal azole compound upon elimination of said group in vivo. The composition of the present invention is stable and usable particularly as a pharmaceutical preparation for an injection composition.

15 Claims, No Drawings

ANTIMYCOTIC DRUG COMPOSITION

This application is the National Stage of International Application No. PCT/JP99/05292, filed on Sep. 28, 1999.

TECHNICAL FIELD

The present invention relates to a composition comprising a novel azole-based compound having an anti-fungal action and a saccharide, which is used in the fields of medicine etc.

BACKGROUND ART

Various azole compounds having an antifungal action have hitherto been known. For example, Japanese Patent Kokai Publication No. Hei 6-293740 discloses an azole compound represented by the formula:

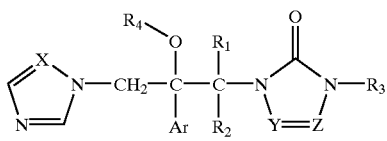

(wherein Ar is a substituted phenyl group; $R_1$ and $R_2$ independently are a hydrogen atom or a lower alkyl group, or $R_1$ and $R_2$ may combine together to form a lower alkylene group; $R_3$ is a group bonded through a carbon atom; $R_4$ is a hydrogen atom or an acyl group; X is a nitrogen atom or a methine group; and Y and Z independently are a nitrogen atom or a methine group which may optionally be substituted with a lower alkyl group) or a salt thereof. Japanese Patent Kokai Publication No. Hei 8-104676 discloses a compound represented by the formula:

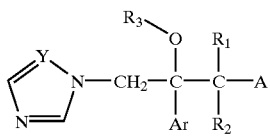

(wherein Ar is an optionally substituted phenyl; $R_1$ and $R_2$ are, the same or different, a hydrogen atom or a lower alkyl group, or $R_1$ and $R_2$ may combine together to form a lower alkylene group; $R_3$ is a hydrogen atom or an acyl group; Y is a nitrogen atom or a methine group; and A is an optionally-substituted saturated cyclic amide group bonded through a first nitrogen atom) and a salt thereof. WO 9625410 $A_1$ (corresponding to Japanese Patent Kokai Publication No. Hei 9-183769) discloses a compound represented by the formula:

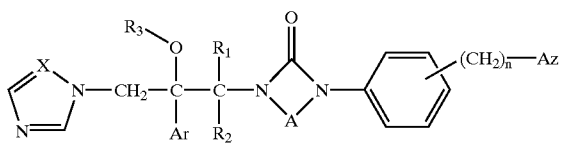

[wherein Ar is an optionally substituted phenyl group; $R_1$ and $R_2$, the same or different, are a hydrogen atom or a lower alkyl group, or $R_1$ and $R_2$ may combine together to form a lower alkylene group; $R_3$ is a hydrogen atom or an acyl group; X is a nitrogen atom or a methine group; A is Y=Z (Y and Z, the same or different, are a nitrogen atom or a methine group optionally substituted with a lower alkyl group) or an ethylene group optionally substituted with a lower alkyl group; n is an integer of 0 to 2; and Az is an optionally substituted azolyl group] or a salt thereof.

On the other hand, a series of compounds referred to as a soft drug have hitherto been known as a quaternary ammonium salt type derivative of an azole (imidazole, triazole) compound which is hydrolyzed enzymatically and/or non-enzymatically. For example, quaternary ammonium salt derivatives of 1-methylimidazole are reported in Journal of Medicinal Chemistry, Vol. 23, page 469, 1980 (antibacterial activity), ibid., Vol. 23, 566, 1980 (antitumor activity), ibid., Vol. 23, 474, 1980 (anticholinergic activity) and ibid., Vol. 32, 493, 1989 (acetylcholine esterase reactivation activity), and these quaternary salts themselves have a biological activity and it is one of their features that hydrolysis thereof occurs rapidly. On the other hand, a quaternary ammonium salt type derivative of azole compounds as a kind of prodrug has been reported only in Pharmaceutical Research Vol. 9, page 372, 1992 (antiglaucoma drug) and Entomologia Experimentalis et Aplicata, Vol. 44, page 295, 1987 (insecticide). In addition, an example of use as a synthetic intermediate of a quaternary ammonium type derivative of imidazole, utilizing its easily hydrolysable property, is reported in Journal of Chemical Society Perkin I, page 1341, 1979 and New Journal of Chemistry, Vol. 16, page 107, 1992. Moreover, a series of quaternary ammonium salt type-derivatives are described in U.S. Pat. Nos. 4,061,722 and 4,160,099. However, enzymatically and/or non-enzymatically hydrolyzed quaternary salt derivatives of the azole compounds having an antifungal activity have never been known.

These azole-based compounds having an anti-fungal action are neither necessarily sufficient in respect of their solubility in e.g. water for use as injection nor sufficiently satisfactory in respect of the absorption thereof into a living body for demonstrating a high therapeutic effect, and thus there is a need for improvements in the solubility thereof in water and for improvements in the absorption thereof into a living body. Further, there is a need for a pharmaceutical preparation for injection stably containing an azole compound having an anti-fungal action.

DISCLOSURE OF INVENTION

As a result of their extensive study under the circumstances described above, the present inventors found that those derivatives derived from azole-based compounds by quaternarizing nitrogen atoms contained in 1H-imidazole-1-yl group or 1H-1,2,4-triazole-1-yl group thereof have improved solubility in water and are hydrolyzed enzymatically and/or non-enzymatically in vivo to form those compounds having 1H-imidazole-1-yl group or 1H-1,2,4-triazole-1-yl group and having an anti-fungal activity, that the stability of said compounds is improved by adding saccharides to said compounds, and that lyophilization of compositions containing said compounds and saccharides can give rise to further stable lyophilized products, and on the basis of these findings, the present invention was completed.

That is, the present invention relates to:

(1) A composition comprising a quaternized nitrogen-containing imidazole-1-yl or 1,2,4-triazole-1-yl compound wherein one of the nitrogen atoms constituting the azole ring is quaternized with a group eliminating in vivo and represented by the formula:

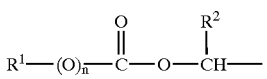

wherein $R^1$ represents a hydrocarbon or heterocyclic group which may be substituted, $R^2$ represents a hydrogen atom or a lower alkyl group, and n is 0 or 1, and a saccharide, said compound being capable of being converted into an anti-fungal azole compound upon elimination of said group in vivo;

(2) The composition according to item (1) above, which is a lyophilized product;

(3) The composition according to item (1) or (2) above, wherein the quaternized nitrogen-containing imidazole-1-yl or 1,2,4-triazole-1-yl compound is a compound represented by the formula:

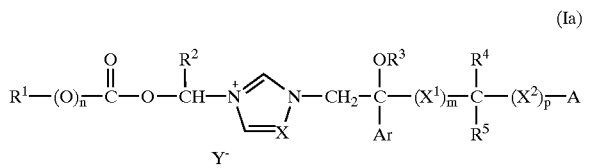

wherein X represents a nitrogen atom or a methine group, Ar represents a phenyl group which may be substituted, A represents a hydrocarbon or heterocyclic group which may be substituted, $X^1$ represents an oxygen atom or a methylene group, $X^2$ represents a sulfur atom which may be oxidized, m and p each represents 0 or 1, and $Y^-$ represents an anion, (1) $R^3$, $R^4$ and $R^5$ are the same or different and each represents a hydrogen atom or a lower alkyl group, (2) $R^3$ represents a hydrogen atom or a lower alkyl group, and $R^4$ and $R^5$ are combined to form a lower alkylene group, or (3) $R^5$ represents a hydrogen atom or a lower alkyl group, and $R^3$ and $R^4$ are combined to form a lower alkylene group, and other symbols have the same meanings as defined above;

(4) The composition according to item (1) or (2) above, wherein the quaternized nitrogen-containing imidazole-1-yl or 1,2,4-triazole-1-yl compound is 4-acetoxymethyl-1-[(2R,3R)-2-(2,4-difluorophenyl)-2-hydroxy-3-[2-oxo-3-[4-(1H-tetrazol-1-yl)phenyl]-1-imidazolydinyl]butyl]-1H-1,2,4-triazolium chloride;

(5) The composition according to item (1) or (2) above, which is an anti-fungal agent;

(6) The composition according to item (1) or (2) above, wherein the saccharide is a monosaccharide, a disaccharide or sugar alcohol;

(7) The composition according to item (1) or (2) above, wherein the saccharide is fructose, glucose, maltose, cellobiose, gentiobiose, melibiose, lactose, turanose, sophorose, trehalose, isotrehalose, isosaccharose, white sugar, mannitol, sorbitol, xylitol or inositol;

(8) The composition according to item (1) or (2) above, wherein the saccharide is maltose, lactose, white sugar, mannitol, trehalose or inositol;

(9) The composition according to item (1) or (2) above, wherein the saccharide is inositol or trehalose;

(10) The composition according to item (1) or (2) above, wherein the saccharide is contained in an amount of 0.001 to 1000 parts by weight per 1 part by weight of the quaternized nitrogen-containing imidazole-1-yl or 1,2,4-triazole-1-yl compound;

(11) The composition according to item (1) or (2) above, wherein the saccharide is contained in an amount of 0.01 to 100 parts by weight per 1 part by weight of the quaternized nitrogen-containing imidazole-1-yl or 1,2,4-triazole-1-yl compound;

(12) The composition according to item (1) or (2) above, wherein the saccharide is contained in an amount of 0.1 to 10 parts by weight per 1 part by weight of the quaternized nitrogen-containing imidazole-1-yl or 1,2,4-triazole-1-yl compound;

(13) The composition according to item (1) or (2) above, which is a pharmaceutical preparation for injection;

(14) A process for producing a lyophilized product, which comprises adding a saccharide to an aqueous solution of a quaternized nitrogen-containing imidazole-1-yl or 1,2,4-triazole-1-yl compound wherein one of the nitrogen atoms constituting the azole ring is quaternized with a group of formula (II) eliminating in vivo, and then lyophilizing the mixture, said compound being capable of being converted into an anti-fungal azole compound upon elimination of said group in vivo;

(15) A method of stabilizing a quaternized nitrogen-containing imidazole-1-yl or 1,2,4-triazole-1-yl compound in a lyophilized product, which comprises adding a saccharide to an aqueous solution of a quaternized nitrogen-containing imidazole-1-yl or 1,2,4-triazole-1-yl compound wherein one of the nitrogen atoms constituting the azole ring is quaternized with a group of formula (II) eliminating in vivo, and then lyophilizing the mixture, said compound being capable of being converted into an anti-fungal azole compound upon elimination of said group in vivo;

(16) Use of a saccharide as an additive in a composition for stabilizing a quaternized nitrogen-containing imidazole-1-yl or 1,2,4-triazole-1-yl compound wherein one of the nitrogen atoms constituting the azole ring is quaternized with a group of formula (II) eliminating in vivo, said compound being capable of being converted into an anti-fungal azole compound upon elimination of said group in vivo; and

(17) Use of a composition for production of a pharmaceutical preparation for injection, said composition comprising a quaternized nitrogen-containing imidazole-1-yl or 1,2,4-triazole-1-yl compound wherein one of the nitrogen atoms constituting the azole ring is quaternized with a group of formula (II) eliminating in vivo, and a saccharide, said compound being capable of being converted into an anti-fungal azole compound upon elimination of said group in vivo.

The "quaternized nitrogen-containing imidazole-1-yl or 1,2,4-triazole-1-yl compound wherein one of the nitrogen atoms constituting the azole ring is quaternized with a group of formula (II) eliminating in vivo, said compound being capable of being converted into an anti-fungal azole compound upon elimination of said group in vivo" (also referred to hereinafter as compound (I)) is a compound having an imidazole-1-yl or 1,2,4-triazole-1-yl group in the molecule, wherein a nitrogen atom at the 3-position in the imidazole-1-yl group, or a nitrogen atom at the 2- or 4-position in the 1,2,4-triazole-1-yl group, is quaternized with the group of formula (II) present at said nitrogen atom, said compound being capable of being converted, upon hydrolysis and removal of said group in vivo, into an anti-fungal compound having a quaternized nitrogen atom-free imidazole-1-yl or 1,2,4-triazole-1-yl group.

Examples of such a compound include a compound represented by the formula (Ia) or a salt thereof [hereinafter referred to as a compound (Ia), sometimes].

Examples of the "hydrocarbon group" of the "optionally substituted hydrocarbon group" represented by $R^1$ includes aliphatic hydrocarbon group, aromatic hydrocarbon group and aromatic-aliphatic hydrocarbon group. Examples of the aliphatic hydrocarbon group include alkyl group, cycloalkyl group, cycloalkylalkyl group, alkenyl group and alkynyl group. Examples of the alkyl group include straight-chain or branched alkyl group having 1 to 20 carbon atoms, such as methyl, ethyl, n-propyl, isopropyl, n-butyl, isobutyl, sec-butyl, tert-butyl, pentyl, hexyl, heptyl, octyl, nonyl, decyl, dodecyl, etc., and among them, lower alkyl group having 1 to 6 carbon atoms (e.g. methyl, ethyl, n-propyl, isopropyl, n-butyl, isobutyl, sec-butyl, tert-butyl, etc.) is particularly preferable. Examples of the cycloalkyl group include cycloalkyl group having 3 to 10 carbon atoms, such as cyclopropyl, cyclobutyl, cyclopentyl, cyclohexyl, cycloheptyl, cyclooctyl, adamantyl, etc., and among them, cycloalkyl group having 3 to 6 carbon atoms (e.g. cyclopropyl, cyclobutyl, cyclopentyl, cyclohexyl, etc.) is particularly preferable. Examples of the cycloalkylalkyl group include those having 4 to 12 carbon atoms, such as cyclopropylmethyl, cyclopentylmethyl, cyclohexylmethyl, etc., and among them, cycloalkylalkyl group having 6 to 8 carbon atoms (e.g. cyclopentylmethyl, cyclohexylmethyl, etc.) is particularly preferable. Examples of the alkenyl group include those having 2 to 4 carbon atoms, such as vinyl, propenyl, butenyl, etc., and among them, alkenyl having 2 to 3 carbon atoms (e.g. vinyl, propenyl) is particularly preferable. Examples of the alkynyl group include those having 2 to 4 carbon atoms, such as ethynyl, propynyl, butynyl, etc., and among them, alkynyl having 2 to 3 carbon atoms (e.g. ethynyl, propynyl) is particularly preferable.

Examples of the aromatic hydrocarbon group include those having 6 to 14 carbon atoms, such as phenyl, naphthyl, biphenylyl, anthryl, indenyl, etc., and among them, aryl group having 6 to 10 carbon atoms (e.g. phenyl, naphthyl, etc.) is particularly preferable.

Examples of the aromatic-aliphatic hydrocarbon group include aralkyl groups having 7 to 15 carbon atoms, such as benzyl, phenethyl, phenylpropyl, naphthylmethyl, indanyl, indanylmethyl, 1,2,3,4-tetrahydronaphthyl, 1,2,3,4-tetrahydronaphthylmethyl, etc., and among them, aralkyl groups having 7 to 11 carbon atoms (e.g. benzyl, phenethyl, naphthyl-methyl, etc.,) are particularly preferable.

The "heterocyclic group" of the "optionally substituted heterocyclic group" represented by $R^1$ is a group obtained by removing one of hydrogen atoms linked to a heterocyclic ring, and such a heterocyclic ring represents a 5- to 8-membered ring containing 1 to several, preferably 1 to 4 hetero atoms (e.g. nitrogen atom (optionally oxidized), oxygen atom, sulfur atom, etc.), or a condensed ring thereof. Specific examples of the heterocyclic ring group include pyrrolyl, pyrazolyl, imidazolyl, 1,2,3-triazolyl, 1,2,4-triazolyl, tetrazolyl, furyl, thienyl, oxazolyl, isoxazolyl, 1,2, 3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2, 4-thiadiazolyl, 1,2,5-thiadiazolyl, 1,3,4-thiadiazolyl, pyrrolidinyl, pyridyl, pyridazinyl, pyrimidinyl, pyrazinyl, piperidinyl, piperazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridinyl, thieno[2,3-d] pyridyl, benzopyranyl, tetrahydrofuryl, tetrahydropyranyl, dioxolanyl, dioxanyl and the like.

Examples of the substituent in the "optionally substituted hydrocarbon group" and "optionally substituted heterocyclic group" represented by $R^1$ include heterocyclic group, oxo group, hydroxy group, $C_{1-6}$ alkoxy group, $C_{3-10}$ cycloalkyloxy group, $C_{6-10}$ aryloxy group, $C_{7-19}$ aralkyloxy group, heterocyclic ring-oxy group, mercapto group, $C_{1-6}$ alkylthio group (sulfur atom may be oxidized), $C_{3-10}$ cycloalkylthio group (sulfur atom may be oxidized), $C_{6-10}$ arylthio group (sulfur atom may be oxidized), $C_{7-19}$ aralkylthio group (sulfur atom may be oxidized), a heterocyclic ring-thio group, a heterocyclic ring-sulfinyl group, a heterocyclic ring-sulfonyl group, an amino group, mono-$C_{1-6}$ alkylamino group, di-$C_{1-6}$ alkylamino group, tri-$C_{1-6}$ alkylammonio group, $C_{3-10}$ cycloalkylamino group, $C_{6-10}$ arylamino group, $C_{7-19}$ aralkylamino group, heterocyclic ring-amino group, cyclic amino group, nitro group, halogen atom, cyano group, carboxyl group, $C_{1-10}$ alkoxy-carbonyl group, $C_{6-10}$ aryloxy-carbonyl group, $C_{7-19}$ aralkyloxy-carbonyl group, $C_{6-10}$ aryl-carbonyl group, $C_{1-6}$ alkanoyl group, $C_{3-5}$ alkenoyl group, $C_{6-10}$ aryl-carbonyloxy group, $C_{2-6}$ alkanoyloxy group, $C_{3-5}$ alkenoyloxy group, optionally substituted carbamoyl group, optionally substituted thiocarbamoyl group, optionally substituted carbamoyloxy group, $C_{1-6}$ alkanoylamino group, $C_{6-10}$ aryl-carbonylamino group, $C_{1-10}$ alkoxy-carboxamido group, $C_{6-10}$ aryloxy-carboxamido group, $C_{7-19}$ aralkyloxy-carboxamido group, $C_{1-10}$ alkoxy-carbonyloxy group, $C_{6-10}$ aryloxy-carbonyloxy group, $C_{7-19}$ aralkyloxy-carbonyloxy group, $C_{3-10}$ cycloalkyloxy-carbonyloxy group, optionally substituted ureido group, etc., and they may be the same or different and 1 to 4 substituents may be present. Examples of the "$C_{1-6}$ alkoxy group" include methoxy, ethoxy, n-propoxy, isopropoxy, n-butoxy, tert-butoxy, n-pentyloxy, n-hexyloxy, etc.; "examples of the $C_{3-10}$ cycloalkyloxy group" include cyclopropyloxy, cyclohexyloxy, etc.; examples of the "$C_{6-10}$ aryloxy group" include phenoxy, naphthyloxy, etc.; examples of the "$C_{7-19}$ aralkyloxy group" include benzyloxy, 1-phenylethyloxy, 2-phenylethyloxy, benzhydryloxy, etc.; examples of the "$C_{1-6}$ alkylthio group (sulfur atom may be oxidized)" include methylthio, ethylthio, n-propylthio, n-butylthio, methylsulfinyl, methysulfonyl, etc.; examples of the "$C_{3-10}$ cycloalkylthio group (sulfur atom may be oxidized)" include cyclopropylthio, cyclohexylthio, cyclopentylsulfinyl, cyclohexylsulfonyl, etc.; examples of the "$C_{6-10}$ arylthio group (sulfur atom may be oxidized)" include phenylthio, naphthylthio, phenylsulfinyl, phenylsulfonyl, etc.; examples of the "$C_{7-19}$ aralkylthio group (sulfur atom may be oxidized)" include benzylthio, phenylethylthio, benzhydrylthio, benzylsulfinyl, benzylsulfonyl, etc.; examples of the "mono-$C_{1-6}$ alkylamino group" include methylamino, ethylamino, n-propylamino, n-butylamino, etc.; examples of the "di-$C_{1-6}$ alkylamino group" include dimethylamino, diethylamino, methylethylamino, di-(n-propyl)amino, di-(n-butyl)amino, etc.; examples of the "tri-$C_{1-6}$ alkylammonio groups" include trimethylammonio, etc.; examples of the "$C_{3-10}$ cycloalkylamino group" include cyclopropylamino, cyclopentylamino, cyclohexylamino, etc.; examples of the "$C_{6-10}$ arylamino group" include anilino, N-methylanilino, etc.; examples of the "$C_{7-19}$ aralkylamino group" include benzylamino, 1-phenylethylamino, 2-phenylethylamino, benzhydrylamino, etc.; examples of the "cyclic amino group" include 1-pyrrolidinyl, piperidino, 1-piperazinyl, morpholino, thiomorpholino, etc.; examples of the "halogen atom" include fluorine, chlorine, bromine, iodine, etc.; examples of the "$C_{1-10}$ alkoxy-carbonyl group" include methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl, norbornyloxycarbonyl, etc.; "$C_{6-10}$ aryloxy-carbonyl group" include phenoxycarbonyl, naphthyloxycarbonyl, etc.; examples of the "$C_{7-19}$ aralkyloxy-carbonyl group" include benzyloxycarbonyl, benzhydryloxycarbonyl, etc.; examples of the "$C_{6-10}$ arylcarbonyl group" include benzoyl, naphthoyl, phenylacetyl, etc.; examples of the "$C_{1-6}$ alkanoyl group" include formyl, acetyl, propionyl, butyryl, valeryl, pivaloyl, etc.; examples of the "$C_{3-5}$ alkenoyl group" include acryloyl, crotonoyl, etc.; examples of the "$C_{6-10}$ aryl-carbonyloxy group" include benzoyloxy, naphthoyloxy, phenylacetoxy, etc.; examples of the "$C_{2-6}$ alkanoyloxy group" include acetoxy, propionyloxy, butyryloxy, valeryloxy, pivaloyloxy, etc.; examples of the "$C_{3-5}$ alkenoyloxy group" include acryloyloxy, crotonoyloxy, etc.; examples of the "optionally substituted carbamoyl group" include carbamoyl group which may be substituted with one or two substituents selected from $C_{1-4}$ alkyl group (e.g. methyl, ethyl, etc.), phenyl group, $C_{1-7}$ acyl group (e.g. acetyl, propionyl, benzoyl, etc.) and $C_{1-4}$ alkoxy-phenyl group (e.g. methoxyphenyl, etc.), and cyclic aminocarbonyl group, and specific examples thereof include carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl, N-(p-methoxyphenyl)carbamoyl, 1-pyrrolidinylcarbonyl, piperidinocarbonyl, 1-piperazinylcarbonyl, morpholinocarbonyl, etc.; examples of the "optionally substituted thiocarbamoyl group" include thiocarbamoyl groups which may be substituted by one or two substituents selected from $C_{1-4}$ alkyl group (e.g. methyl, ethyl, etc.) and phenyl group, and specific examples thereof include thiocarbamoyl, N-methylthiocarbamoyl, N-phenylthiocarbamoyl, etc.; examples of the "optionally substituted carbamoyloxy group" include carbamoyloxy groups which may be substituted with one or two substituents selected from $C_{1-4}$ alkyl group (e.g. methyl, ethyl, etc.) and phenyl group, and specific examples thereof include carbamoyloxy, N-methylcarbamoyloxy, N,N-dimethylcarbamoyloxy, N-ethylcarbamoyloxy, N-phenylcarbamoyloxy, etc.; examples of the "$C_{1-6}$ alkanoylamino group" include acetamido, propionamido, butyramido, valelamido, pivalamido, etc.; examples of the "$C_{6-10}$ aryl-carbonylamino group" benzamido, naphthamido, phthalimido, etc.; examples of the "$C_{1-10}$ alkoxy-carboxamido group" include methoxycarboxamido ($CH_3OCONH-$), ethoxycarboxamido, tert-butoxycarboxamido, etc.; examples of the "$C_{6-10}$ aryloxycarboxamido group" include phenoxycarboxamido ($C_6H_5OCONH-$), etc.; examples of the "$C_{7-10}$ aralkyloxycarboxamido group" include benzyloxycarboxamido ($C_6H_5CH_2OCONH-$), benzhydryloxycarboxamido, etc.; examples of the "$C_{1-10}$ alkoxy-carbonyloxy group" include methoxycarbonyloxy, ethoxycarbonyloxy, n-propoxycarbonyloxy, isopropoxycarbonyloxy, n-butoxycarbonyloxy, tert-butoxycarbonyloxy, n-pentyloxycarbonyloxy, n-hexyloxycarbonyloxy, etc.; examples of the "$C_{6-10}$ aryloxy-carbonyloxy group" include phenoxycarbonyloxy, naphthyloxycarbonyloxy, etc.; examples of the "$C_{7-19}$ aralkyloxy-carbonyloxy group" include benzyloxycarbonyloxy, 1-phenylethyloxycarbonyloxy, 2-phenylethyloxycarbonyloxy, benzhydryloxycarbonyloxy, etc.; examples of the "$C_{3-10}$ cycloalkyloxy-carbonyloxy group" include cyclopropyloxycarbonyloxy, cyclohexyloxycarbonyloxy, etc.; and examples of the "optionally substituted ureido group" include ureido group which may be substituted with 1 to 3 substituents selected from $C_{1-4}$ alkyl group (e.g. methyl, ethyl, etc.), phenyl group, etc., and specific examples thereof include ureido, 1-methylureido, 3-methylureido, 3,3-dimethylureido, 1,3-dimethylureido, 3-phenylureido, etc.

As the substituent of the "optionally substituted heterocyclic group" represented by $R^1$, for example, $C_{1-6}$ alkyl group, $C_{3-6}$ cycloalkyl group, $C_{4-7}$ cycloalkylalkyl group, $C_{2-3}$ alkenyl group, $C_{2-3}$ alkynyl group, $C_{6-10}$ aryl group, $C_{7-11}$ aralkyl group, etc. are used, in addition to those described above. Examples of the "$C_{1-6}$ alkyl group" include methyl, ethyl, n-propyl, isopropyl, n-butyl, isobutyl, sec-butyl, tert-butyl, etc.; examples of the "$C_{3-6}$ cycloalkyl group" include cyclopropyl, cyclobutyl, cyclopentyl, cyclohexyl, etc.; examples of the "$C_{4-7}$ cycloalkylalkyl group" include cyclopropylmethyl, cyclopentylmethyl, etc.; examples of the "$C_{2-3}$ alkenyl group" include vinyl, propenyl, etc.; examples of the "$C_{2-3}$ alkynyl group" include ethynyl, propynyl, etc.; examples of the "$C_{6-10}$ aryl group" includes phenyl, naphthyl, etc.; and examples of the "$C_{7-11}$ aralkyl group" include benzyl, phenetyl, naphthylmethyl, etc. The number of these substituents of the "optionally substituted hydrocarbon group" and "optionally substituted heterocyclic group" represented by $R^1$ is not limited to one, and the substituents may be the same or different plural (2 to 4) substituents.

The heterocyclic group in the substituent of the "hydrocarbon group" and "heterocyclic group", and the heterocyclic group in the heterocyclic ring-oxy group, heterocyclic ring-thio group, heterocyclic ring-sulfinyl group, heterocyclic ring-sulfonyl group and heterocyclic ring-amino group respectively represent a group obtained by removing one of hydrogen atoms linked to the heterocyclic ring, and such heterocyclic ring represents a 5- to 8-membered ring containing 1 to several, preferably 1 to 4 hetero atoms (e.g. nitrogen atom (optionally oxidized), oxygen atom, sulfur atom, etc.), or a condensed ring thereof. Examples of the heterocyclic group include pyrrolyl, pyrazolyl, imidazolyl, 1,2,3-triazolyl, 1,2,4-triazolyl, tetrazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyrrolidinyl, pyridyl, pyridazinyl, pyrimidinyl, pyrazinyl, piperidinyl, piperazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridinyl, thieno[2,3-d]pyridyl, benzopyranyl, tetrahydrofuryl, tetrahydropyranyl, dioxolanyl, dioxanyl, etc. These heterocyclic group may be substituted with 1 to 3 substituents selected from $C_{1-4}$ alkyl group (e.g. methyl, ethyl, etc.), hydroxyl group, oxo group and $C_{1-4}$ alkoxy group (e.g. methoxy, ethoxy, etc.).

In the optionally substituted hydrocarbon group or heterocyclic group represented by $R^1$, as the "optionally substituted hydrocarbon group", $C_{1-6}$ alkyl group (examples of the $C_{1-6}$ alkyl group include methyl, ethyl, n-propyl, isopropyl, n-butyl, isobutyl, tert-butyl, etc.) which may be substituted with 1 to 3 substituents selected from hydroxyl, $C_{1-6}$ alkoxy group, $C_{7-19}$ aralkyloxy group, $C_{1-6}$ alkylthio group, $C_{1-6}$ alkylsulfonyl, $C_{1-6}$ alkanoylamino group, $C_{1-10}$ alkoxy-carbonyl group, $C_{7-19}$ aralkyloxy-carbonyl group, optionally substituted carbamoyl group, $C_{1-10}$ alkoxy-carboxamido, $C_{7-10}$ aralkyloxy-carboxamido and heterocyclic group (optionally substituted) is preferable, and specific examples thereof include methyl, ethyl, n-propyl, isopropyl, n-butyl, isobutyl, tert-butyl, methoxymethyl, ethoxymethyl, 1-methoxyethyl, 2-methoxyethyl, 1-ethoxyethyl, 2-ethoxyethyl, 2-benzyloxyethyl, 3-benzyloxypropyl, 1,3-dibenzyloxy-2-propyl, hydroxymethyl, 1-hydroxyethyl, 2-hydroxyethyl, 3-hydroxypropyl, 2,3-dihydroxypropyl, 1,3-dihydroxy-2-propyl, methylthiomethyl, methylsulfonylethyl, acetamidomethyl 1-acetamidoethyl, 2-acetamidoethyl, methoxycarbonylmethyl, ethoxycarbonylmethyl, tert-butoxycarbonylmethyl, 1-ethoxycarbonylethyl, 2-ethoxycarbonylethyl, 1-methoxycarbonyl-1-methylethyl, 1-ethoxycarbonyl-1-methylethyl, 1-tert-butoxycarbonyl-1-methylethyl, 1-benzyloxycarbonylethyl, 1-benzyloxycarbonyl-1-methylethyl, carbamoylmethyl, N,N-dimethylcarbamoylmethyl, methoxycarboxamidomethyl, ethoxycarboxamidomethyl, tert-butoxycarboxamidomethyl, benzyloxycarboxamidomethyl, 2-ethoxycarboxamidoethyl, 2-furylmethyl, 2-tetrahydrofurylmethyl, 1,3-dioxolan-2-ylmethyl, 1,3-dioxolan-4-ylmethyl, 2-oxo-1,3-dioxolan-4-ylmethyl, 2,2-dimethyl-1,3-dioxolan-4-ylmethyl, 1,3-dioxan-5-ylmethyl, 1-ethoxycarbonyl-1-(2,3,4-trihydroxyphenyl)methyl, 1-acetamido-2-ethoxycarbonyl, 1-acetamido-3-ethoxycarbonylpropyl, 2-acetamido-2-ethoxycarbonylethyl, 3-acetamido-3-ethoxycarbonylpropyl, 1-acetamido-2-carbamoylethyl, 1-acetamido-3-carbamoylpropyl, etc.

Among the above $C_{1-6}$ alkyl group which may be substituted with 1 to 3 substituents, the most preferable ones include straight-chain or branched $C_{1-4}$ alkyl group, such as methyl, ethyl, n-propyl, isopropyl, n-butyl, isobutyl, tert-butyl, etc.; and straight-chain or branched $C_{1-4}$ alkyl group substituted with hydroxyl group, $C_{1-6}$ alkoxy group, $C_{1-10}$ alkoxy-carbonyl group, heterocyclic group (optionally substituted), etc., such as 2-hydroxyethyl, 3-hydroxypropyl, 2,3-dihydroxypropyl, 1,3-dihydroxy-2-propyl, 2-methoxyethyl, 2-ethoxyethyl, 3-benzyloxypropyl, ethoxycarbonylmethyl, 1-ethoxycarbonylethyl, 1-benzyloxycarbonylethyl, 2-furylmethyl, 2-tetrahydrofurylmethyl, 1,3-dioxolan-4-ylmethyl, 2-oxo-1,3-dioxolan-4-ylmethyl, 2,2-dimethyl-1,3-dioxolan-4-ylmethyl, etc.

In the optionally substituted hydrocarbon group or heterocyclic group represented by $R^1$, as the "optionally substituted heterocyclic group", a heterocyclic group substituted with 1 to 3 substituents selected from oxo group, hydroxyl group, $C_{1-6}$ alkyl group, $C_{1-6}$ alkoxy group, etc. are preferable, and specific examples thereof include furyl, thienyl, pyranyl, thiopyranyl, dioxinyl, dioxolyl, benzopyranyl, tetrahydrofuryl, tetrahydropyranyl, dioxolanyl, dioxanyl, methylfuryl, hydroxyfuryl, methylthienyl, methoxyfuryl, 2-oxo-1,3-dioxolyl, 2,2-dimethyl-1,3-dioxolyl, 2-oxo-1,3-dioxolanyl, 2,2-dimethyl-1,3-dioxolanyl, 2-oxo-1,3-dioxanyl, 2,2-dimethyl-1,3-dioxanyl, etc. Among them, furyl, thienyl, dioxanyl, 2-oxo-1,3-dioxanyl, 2,2-dimethyl-1,3-dioxanyl are particularly preferable.

Examples of the lower alkyl group represented by $R^2$ include lower alkyl group having 1 to 4 carbon atoms (e.g. methyl, ethyl, propyl, isopropyl, butyl, isobutyl, sec-butyl, tert-butyl, etc.), and methyl is particularly preferable.

As $R^2$, a hydrogen atom or methyl is particularly preferable.

X represents a nitrogen atom or a methine group, and a nitrogen atom is preferable.

Examples of the optionally oxidized sulfur atom represented by $X^2$ includes thio, sulfinyl and sulfonyl.

m and p respectively represent an integer of 0 or 1, and the case where both of them are 0 is preferable.

Examples of the substituent in the "optionally substituted phenyl group" represented by Ar include halogen (e.g. fluorine, chlorine, bromine, iodine, etc.), halogenated lower ($C_{1-4}$) alkyl group (e.g. fluoromethyl, trifluoromethyl, chloromethyl, 1-fluoroethyl, 2-fluoroethyl, 1,1-difluoroethyl, 1,2-difluoroethyl, etc.) and halogenated lower ($C_{1-4}$) alkoxy group (e.g. fluoromethoxy, trifluoromethoxy, chloromethoxy, 1-fluoroethoxy, 2-fluoroethoxy, 1,1-difluoroethoxy, 1,2-difluoroethoxy, 1,1,2,2-tetrafluoroethoxy, 2,2,2-trifluoroethoxy, 2,2,3,3-tetrafluoropropoxy, 2,2,3,3,3-pentafluoropropoxy, etc.). The substituent is preferably a halogen (e.g. fluorine, chlorine, bromine, iodine, etc.), more preferably fluorine. The number of substituents is preferably 1 to 3, more preferably 1 to 2.

Preferred examples of Ar include halogenophenyl group, halogenated lower ($C_{1-4}$) alkylphenyl group, halogenated lower ($C_{1-4}$) alkoxyphenyl group, etc. Examples of the halogenophenyl group include 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 2,4,6-trifluorophenyl, 4-bromophenyl, etc. Examples of the halogenated lower ($C_{1-4}$) alkylphenyl group include 4-trifluoromethylphenyl, etc. Examples of the halogenated lower ($C_{1-4}$) alkoxyphenyl group include 4-trifluoromethoxyphenyl, 4-(1,1,2,2-tetrafluoroethoxy)phenyl, 4-(2,2,2-trifluoroethoxy)phenyl, 4-(2,2,3,3-tetrafluoropropoxy)phenyl, 4-(2,2,3,3,3-pentafluoropropoxy)phenyl, etc.

Specific preferable examples of Ar are a phenyl group substituted with 1 to 2 halogens, such as 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 4-bromophenyl, etc. Among them, a phenyl group substituted with 1 to 2 fluorine atoms, such as 4-fluorophenyl, 2-fluorophenyl, 2,4-difluorophenyl, etc. is particularly preferable, and 2-fluorophenyl and 2,4-difluorophenyl are more preferable.

An anion represented by $Y^-$ is that obtained by removing one proton from an organic acid or an inorganic acid, and examples of the organic acid include acetic acid, propionic acid, methanesulfonic acid, benzenesulfonic acid, toluensulfonic acid, trifluoromethanesulfonic acid trifluoroacetic acid, etc., and examples of the inorganic acid include hydrochloric acid, sulfuric acid, phosphoric acid, hydrofluoric acid, hydrobromic acid, hydroiodic acid, water, etc. As $Y^-$, an anion obtained by removing one proton from an inorganic acid is preferable. Among them, an anion obtained by removing one proton from a hydro-halogenoic acid such as hydrochloric acid, hydrofluoric acid, hydrobromic acid, hydroiodic acid, etc. is preferable, and an anion obtained by removing one proton from hydrochloric acid, hydrobromic acid, hydroiodic acid, etc. is particularly preferable. $Y^-$ can be defined as a group having a negative charge, and preferred examples thereof include $Cl^-$, $F^-$, $Br^-$, $I^-$, $HSO_3^-$, $HSO_4^-$, $H_2PO_4^-$, $OH^-$, etc. Among them, $Cl^-$, $F^-$, $Br^-$, $I^-$ are preferable, and $Cl^-$, $Br^-$ and $I^-$ are particularly preferable.

Examples of the lower alkyl group represented by $R^3$, $R^4$ and $R^5$ include straight-chain or branched alkyl group having 1 to 4 carbon atoms, such as methyl, ethyl, propyl, isopropyl, butyl, isobutyl, sec-butyl, tert-butyl, etc. Among them, methyl is particularly preferable.

When $R^3$ and $R^4$, or $R^4$ and $R^5$ are combined to form a lower alkylene group, examples of the lower alkylene group include those having 1 to 4 carbon atoms, such as methylene, ethylene, propylene, butylene, etc. When $R^3$ and $R^4$ are combined to form a lower alkylene group, methylene and ethylene are preferable. When $R^4$ and $R^5$ are combined to form a lower alkylene group, ethylene is preferable.

$R^3$ is preferably a hydrogen atom. Preferably, $R^4$ and $R^5$ are simultaneously hydrogen atoms or methyl groups, or one of them is a hydrogen atom and the other one is a methyl group. More preferably, one of $R^4$ and $R^5$ is a hydrogen atom and the other one is methyl.

Examples of the "optionally substituted hydrocarbon group" or "optionally substituted heterocyclic group" represented by A includes the same one as that described for $R^1$. A is preferably a group of the formula:

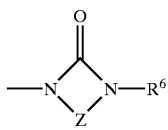

(wherein $R^6$ represents an optionally substituted hydrocarbon group or aromatic heterocyclic group; and Z represents an optionally substituted lower alkylene group or a group of the formula:

—D=E—

(D and E may be same or different and represent a nitrogen atom or a methine group which may be substituted with a lower alkyl)). Examples of the hydrocarbon group in the "optionally substituted hydrocarbon group" represented by $R^6$ include aliphatic hydrocarbon group, aromatic hydrocarbon group and aromatic-aliphatic hydrocarbon group.

Examples of the aliphatic hydrocarbon group include alkyl, cycloalkyl, alkenyl, alkynyl group, etc. Examples of the alkyl groups include straight-chain or branched one having 1 to 12 carbon atoms. Specific examples thereof include methyl, ethyl, n-propyl, isopropyl, n-butyl, isobutyl, sec-butyl, tert-butyl, heptyl, octyl, nonyl, decyl, dodecyl, etc. Among them, a lower alkyl group having 1 to 4 carbon atoms (e.g. methyl, ethyl, n-propyl, isopropyl, n-butyl, isobutyl, sec-butyl, tert-butyl, etc.) is particularly preferable. Examples of the cycloalkyl groups include cycloalkyl groups having 3 to 8 carbon atoms. Specific examples thereof include cyclopropyl, cyclobutyl, cyclopentyl, cyclohexyl, cycloheptyl, cyclooctyl, etc. Among them, a cycloalkyl group having 3 to 6 carbon atoms (e.g. cyclopropyl, cyclobutyl, cyclopentyl, cyclohexyl, etc.) is particularly preferable. Examples of the alkenyl group include alkenyl group having 2 to 4 carbon atoms. Specific examples thereof include vinyl, propenyl, butenyl, etc. Among them, an alkenyl group having 2 to 3 carbon atoms (e.g. vinyl, propenyl, etc.) is particularly preferable. Examples of the alkynyl group include alkynyl group having 2 to 4 carbon atoms. Specific examples thereof include ethynyl, propynyl, butynyl, etc. Among them, an alkynyl group having 2 to 3 carbon atoms (e.g. ethynyl, propynyl, etc.) is particularly preferable.

Examples of the aromatic hydrocarbon group include aryl group having 6 to 14 carbon atoms. Examples of the aryl group include phenyl, naphthyl, biphenylyl, anthryl, indenyl, etc. Among them, an aryl group having 6 to 10 carbon atoms (e.g. phenyl, naphthyl, etc.) is particularly preferable.

Examples of the aromatic-aliphatic hydrocarbon group include arylalkyl group having 7 to 15 carbon atoms. Specific examples thereof include benzyl, phenetyl, phenylpropyl, naphthylmethyl, indanyl, indanylmethyl, 1,2,3,4-tetrahydronaphthyl, 1,2,3,4-tetrahydronaphthylmethyl, biphenylylmethyl, benzhydryl, etc. Among them, an aralkyl group having 7 to 11 carbon atoms (e.g. benzyl, phenetyl, naphthylmethyl, etc.) is particularly preferable.

Examples of the aromatic heterocyclic group in the "aromatic heterocyclic group which may have a substituent" represented by $R^6$ include aromatic heterocyclic group containing at least one hetero atom selected from nitrogen atom, sulfur atom and oxygen atom. The aromatic heterocyclic group may be condensed with a benzene ring, or 5- or 6-membered heterocyclic ring. Examples of the aromatic heterocyclic group include aromatic heterocyclic group such as imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyl, isooxazolyl, etc.; and condensed aromatic heterocyclic group such as benzimidazolyl, imidazopyrimidinyl, imidazopyridinyl, imidazopyrazinyl, imidazopyridazinyl, benzothiazolyl, quinolyl, isoquinolyl, quinazolinyl, indolyl, etc. As the aromatic heterocyclic group, a 5- or 6-membered aromatic heterocyclic group containing 1 to 3 hetero atoms selected optionally from nitrogen atom, sulfur atom and oxygen atom (e.g. imidazolyl, triazolyl, thiazolyl, thiadiazolyl, thienyl, furyl, pyridyl, pyrimidinyl, etc.) is particularly preferable.

Examples of the substituent in the "aliphatic, aromatic or aromatic-aliphatic hydrocarbon group which may have a substituent, or aromatic heterocyclic group which may have a substituent" represented by $R^6$ include hydroxyl group, optionally esterified carboxyl group (e.g. carboxyl, alkoxycarbonyl having 1 to 6 carbon atoms, such as methoxycarbonyl, ethoxycarbonyl, butoxycarbonyl, etc.), nitro group, amino group, acylamino group (e.g. alkanoylamino having 1 to 10 carbon atoms, such as acetylamino, propionylamino, butyrylamino, etc.), amino group which is mono- or di-substituted with an alkyl group having 1 to 10 carbon atoms (e.g. methylamino, dimethylamino, diethylamino, dibutylamino, etc.), optionally substituted 5- to 6-membered cyclic amino group (e.g. pyrrolidinyl, morpholino, piperidino, pyrazolidinyl, perhydroazepinyl, piperazinyl, 4-benzylpiperazinyl, 4-acetylpiperazinyl, 4-(4-trifluoromethoxyphenyl)-1-piperazinyl, 4-[4-(1,1,2,2-tetrafluoroethoxy)phenyl]-1-piperazinyl, 4-[4-(2,2,3,3-tetrafluoropropoxy)phenyl]-1-piperazinyl, 4-[4-(2,2,2-trifluoroethoxy)phenyl]-1-piperazinyl, 4-[4-(2.2,3,3,3-pentafluoropropoxy)phenyl]-1-piperazinyl, 4-(4-trifluoromethylphenyl)-4-piperazinyl, etc.), alkoxy group having 1 to 6 carbon atoms (e.g. methoxy, ethoxy, propoxy, butoxy, etc.), halogen atom (e.g. fluorine, chlorine, bromine, etc.), alkyl group having 1 to 6 carbon atoms (e.g. methyl, propyl, butyl, etc.), cycloalkyl group having 3 to 6 carbon atoms (e.g. cyclopropyl, cyclopentyl, etc.), halogeno-alkyl group having 1 to 6 carbon atoms (e.g. trifluoromethyl, dichloromethyl, trifluoroethyl, etc.), halogeno-alkoxy group having 1 to 6 carbon atoms (e.g. trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5-octafluoropentoxy, 2-fluoroethoxy, etc.), oxo group, thioxo group, mercapto group, alkylthio group having 1 to 6 carbon atoms (e.g. methylthio, ethylthio, butylthio, etc.), alkylsulfonyl group having 1 to 6 carbon atoms (e.g. methanesulfonyl, ethanesulfonyl, butanesulfonyl, etc.), alkanoyl group having 1 to 10 carbon atoms (e.g. acetyl, formyl, propionyl, butyryl, etc.), 5- or 6-membered aromatic heterocyclic group (e.g. pyrrolyl, pyrazolyl, imidazolyl, 1,2,3-triazolyl, 1,2,4-triazolyl, tetrazolyl, thiazolyl, isothiazolyl, oxazolyl, isoxazolyl, furazanyl, 1,3,4-thiadiazolyl, 1,2,3-thiadiazolyl, 1,2,5-thiadiazolyl, 1,2,4-thiadiazolyl, thienyl, furyl, pyridyl, pyrimidinyl, pyridazinyl, etc.) and condensed aromatic heterocyclic group (e.g. benzimidazolyl, imidazopyrimidinyl, imidazopyridinyl, imidazopyrazinyl, imidazopyridazinyl, benzothiazolyl, quinolyl, isoquinolyl, quinazolyl, indolyl, etc.). Among them, a halogeno-alkoxy group having 1 to 6 carbon atoms and 5-membered aromatic heterocyclic group is preferable, and 1,1,2,2-tetrafluoroethoxy, 2,2,3,3-tetrafluoropropoxy, pyrazolyl (e.g. 1H-pyrazol-1-yl), imidazolyl (e.g. 1H-imidazol-1-yl), 1,2,3-triazolyl (e.g. 1H-1,2,3-triazol-1-yl, 2H-1,2,3-triazol-2-yl), 1,2,4-triazolyl (e.g. 1H-1,2,4-triazol-1-yl), tetrazolyl (e.g. 1H-tetrazol-1-yl, 2H-tetrazol-2-yl) are particularly preferable.

The number of the above substituents is preferably 1 to 3, more preferably 1 to 2.

The aliphatic, aromatic or aromatic-aliphatic hydrocarbon groups which may have a substituent, or aromatic heterocyclic group which may have a substituent, which is represented by $R^6$, is preferably an aromatic hydrocarbon group which may have a substituent, more preferably a phenyl group having a substituent. Among them, a phenyl group substituted with a halogeno-alkoxy group having 1 to 6 carbon atoms (e.g. 4-(1,1,2,2-tetrafluoroethoxy)phenyl, 4-(2,2,3,3-tetrafluoropropoxy)phenyl) and a phenyl group substituted with a 5-membered aromatic heterocyclic group [e.g. 4-(1H-pyrazol-1-yl)phenyl, 4-(1H-imidazol-1-yl)phenyl, 4-(1H-1,2,3-triazol-1-yl)phenyl, 4-(2H-1,2,3-triazol-2-yl)phenyl, 4-(1H-1,2,4-triazol-1-yl)phenyl, 4-(1H-tetrazol-1-yl)phenyl, 4-(2H-tetrazol-2-yl)phenyl] are particularly preferable.

The lower alkylene group in the "optionally substituted lower alkylene group" represented by Z include those having 1 to 3 carbon atoms, such as methylene, ethylene, propylene, etc. Among them, ethylene is particularly preferable. The substituent in the "optionally substituted lower alkylene group" is preferably a straight-chain or branched alkyl group having 1 to 4 carbon atoms, such as methyl, ethyl, n-propyl, isopropyl, n-butyl, isobutyl, sec-butyl, tert-butyl, etc. Among them, methyl and ethyl are more preferable, and methyl is particularly preferable.

Preferred examples of the ethylene group which may be substituted with a lower alkyl group, which is represented by Z, include ethylene, 1-methylethylene, 1,1-dimethylethylene, 1,2-dimethylethylene, 1-ethylethylene, 1,2-diethylethylene, etc. Among them, ethylene is particularly preferable.

When Z is D=E, examples of lower alkyl group in the "methine group which may be substituted with a lower alkyl group" represented by D or E include straight-chain or branched alkyl group having 1 to 4 carbon atoms (e.g. methyl, ethyl, n-propyl, isopropyl, n-butyl, isobutyl, sec-butyl, tert-butyl, etc.). Among them, methyl is preferable.

Preferred examples of the methine group which may be substituted with a lower alkyl group, represented by D or E, include methine, ethylidyne (—C(CH$_3$)=), propylidyne (—C(CH$_2$CH$_3$)=), butylidyne (—C(CH$_2$CH$_2$CH$_3$)=), etc. Among them, methine and ethylident are preferable, and methine is particularly preferable.

The case where one of D and E is a nitrogen atom and the other is methine; the case where both of D and E are methines; the case where both of D and E are nitrogen atoms; and the case where one of D and E is a nitrogen atom and the other is ethylidyne are preferable. Among them, the case where one of D and E is a nitrogen atom and the other one is methine; and the case where both of D and E are methines are particularly preferable.

Specifically, Z is preferably —N=CH—, —CH=N—, —CH=CH—, —N=N—, —N=C(CH$_3$)—, —C(CH$_3$)=N—, —CH$_2$—CH$_2$—, etc. Among them, —N=CH—, —CH=N—, —CH=CH—, —CH$_2$—CH$_2$—, etc. are more preferable, and —N=CH—, —CH$_2$—CH$_2$— are the most preferable.

As the group represented by the formula:

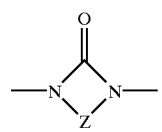

for example,

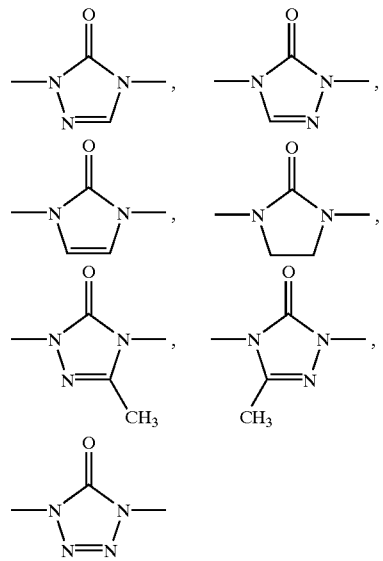

etc. are preferable. Among them,

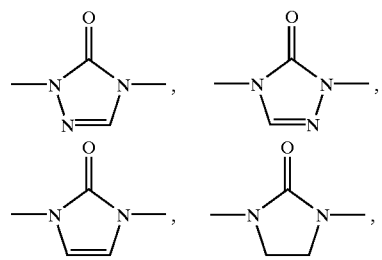

etc. are particularly preferable.

Also, when a reactive atom such as nitrogen atom is present in the optionally substituted hydrocarbon group or optionally substituted heterocyclic group represented by A, a group of formula (II) may be linked to the atom.

When the compound (I) has one or more asymmetric carbon atoms in the molecule, two or more stereoisomers exist, and the stereoisomers and a mixture thereof are also included in the Compound (I).

In the compound represented by the general formula (1a), when A is

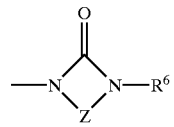

wherein each symbol has the meanings given above, m and p are both 0, $R^4$ is a hydrogen atom and $R^5$ is a methyl group, an optically active compound in which both carbon to which the optionally substituted phenyl group represented by Ar is linked and carbon to which $R^5$ is linked are in the (R) configuration, is particularly preferable.

The formula (Ia) can also be represented by the formula:

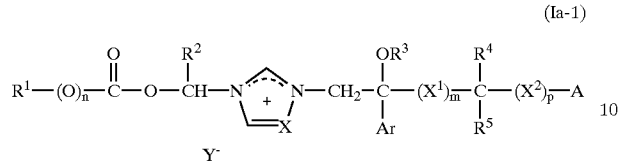

(Ia-1)

(wherein each symbol is as defined above).

The compounds used in the present invention can be either a hydrate or a nonhydrate.

The compounds used in the present invention are converted in vivo into compounds having an antifungal activity, represented by the formula:

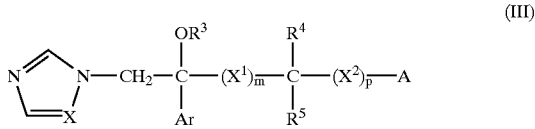

(III)

(wherein each symbol is as defined above)[hereinafter referred to as Compound (III)].

Specific examples of the compounds used in the present invention are shown in Table 1, but are not limited to the exemplified compounds.

TABLE 1

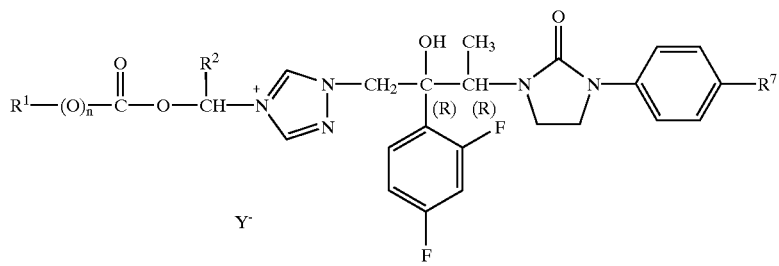

| Compound No. | $R^1$ | n | $R^2$ | Y | $R^7$ |
|---|---|---|---|---|---|
| 1 | $(CH_3)_3C$ | 0 | H | Cl | ![1,2,3-triazolyl] |
| 2 | $(CH_3)_3C$ | 0 | H | Cl | ![tetrazolyl] |
| 3 | $CH_3$ | 0 | H | Cl | ![1,2,3-triazolyl] |
| 4 | $(CH_3)_2CH$ | 0 | H | Cl | ![1,2,3-triazolyl] |
| 5 | $(CH_3)_2CH$ | 0 | H | Cl | ![tetrazolyl] |
| 6 | $CH_3CH_2$ | 1 | $CH_3$ | Cl | ![1,2,3-triazolyl] |
| 7 | $CH_3CH_2$ | 1 | $CH_3$ | Cl | ![tetrazolyl] |

TABLE 1-continued

![Structure: R¹—(O)ₙ—C(=O)—O—CH(R²)—N⁺(triazole)—CH₂—C(R)(OH)(2,4-difluorophenyl)—CH(R)(CH₃)—N(imidazolidinone)—N—phenyl-R⁷, Y⁻]

| Compound No. | R¹ | n | R² | Y | R⁷ |
|---|---|---|---|---|---|
| 8 | $(CH_3)_3C$ | 0 | H | Cl | 1-methyl-triazolium-CH₂-O-C(=O)-C(CH₃)₃, Cl⁻ |
| 9 | $(CH_3)_2CH$ | 1 | H | Cl | 1-methyl-1,2,3-triazole |
| 10 | $CH_3$ | 0 | H | Br | 1-methyl-1,2,3-triazole |
| 11 | $CH_3$ | 0 | H | Br | 1-methyl-tetrazole |
| 12 | $CH_3$ | 0 | H | Cl | 1-methyl-tetrazole |
| 13 | $CH_3CH_2$ | 0 | H | Cl | 1-methyl-1,2,3-triazole |
| 14 | $CH_3CH_2$ | 0 | H | Cl | 1-methyl-tetrazole |
| 15 | $CH_3CH_2$ | 1 | H | Cl | 1-methyl-1,2,3-triazole |
| 16 | $CH_3CH_2$ | 1 | H | Cl | 1-methyl-tetrazole |
| 17 | $CH_3CH_2$ | 1 | H | I | 1-methyl-tetrazole |
| 18 | $(CH_3)_2CH$ | 1 | H | Cl | 1-methyl-tetrazole |

TABLE 1-continued

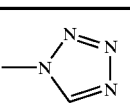

| Compound No. | R¹ | n | R² | Y | R⁷ |
|---|---|---|---|---|---|
| 19 | CH₃CH₂CH₂ | 1 | H | Cl | tetrazolyl |
| 20 | CH₃CH₂CH₂ | 1 | H | I | tetrazolyl |
| 21 | tetrahydrofuran-2-ylmethyl | 1 | H | Cl | tetrazolyl |
| 22 | 5-methyl-1,3-dioxan-5-yl | 1 | H | Cl | tetrazolyl |
| 23 | CH₃CH₂O—C(O)—CH(CH₃)— (S) | 1 | H | Cl | tetrazolyl |
| 24 | PhCH₂OC(O)—CH(CH₃)— (S) | 1 | H | Cl | tetrazolyl |
| 25 | PhCH₂O—(CH₂)₃— | 1 | H | Cl | tetrazolyl |
| 26 | HO—(CH₂)₃— | 1 | H | Cl | tetrazolyl |
| 27 | 2,2-dimethyl-1,3-dioxolan-4-yl-CH₂— (S) | 1 | H | Cl | tetrazolyl |
| 28 | HO—CH₂—CH(OH)—CH₂— (S) | 1 | H | Cl | tetrazolyl |
| 29 | PhCH₂OC(O)(CH₂)₃— | 1 | H | Cl | tetrazolyl |

TABLE 1-continued

[Structure: R¹—(O)ₙ—C(=O)—O—CH(R²)—N⁺(triazole)—CH₂—C(OH)(2,4-difluorophenyl)(R)—CH(CH₃)(R)—N(imidazolidinone with N-aryl-R⁷)  Y⁻]

| Compound No. | R¹ | n | R² | Y | R⁷ |
|---|---|---|---|---|---|
| 30 | tetrahydrofuran-2-yl-CH₂— | 1 | H | I | tetrazol-1-yl |
| 31 | (1,3-dioxan-5-yl with methyl)— | 1 | H | I | tetrazol-1-yl |
| 32 | C₆H₅—CH₂OC(=O)(CH₂)₃— | 1 | H | I | tetrazol-1-yl |
| 33 | HOC(=O)(CH₂)₃— | 1 | H | Cl | tetrazol-1-yl |
| 34 | CH₃C(=O)NH(CH₂)₂— | 1 | H | Cl | tetrazol-1-yl |
| 35 | CH₃O(CH₂)₃— | 1 | H | Cl | tetrazol-1-yl |

36

[Structure: CH₃·C(=O)—O·CH₂—N⁺(triazole)—CH₂—C(OH)(2,4-difluorophenyl)(R)—CH(CH₃)(R)—N(triazolone)—N-C₆H₄—OCH₂CF₂CF₂H  Cl⁻]

The compounds used in the present invention can be produced by introducing a group, which is capable of being eliminated in vivo, into an antifungal compound having an imidazol-1-yl group or 1,2,4-triazol-1-yl group.

Examples of the antifungal compound having an imidazol-1-yl group or 1,2,4-triazol-1-yl group include known azole antifungal compounds such as miconazole, ketoconazole, fluconazole, itraconazole, saperconazole, clotrimazole, D0870, voriconazole, econazole, isoconazole, sulconazole, butoconazole, tioconazole, bifonazole, croconazole, oxiconazole, terconazole, SSY-726, KP-103, Sch-56592, Sch-51048, UR-9746, MFB-1041, UR-9751, UR-9728, UR-9825, ER-30346, T-8581, BAY-W-9279, fenticonazole, omoconazole, flutrimazole, eberconazole, lanoconazole, neticonazole, sertaconazole, genaconazole, etc., but are not limited to known antifungal agents.

The compound (Ia) can be produced, for example, by reacting a compound (III) with a compound represented by the formula (IV):

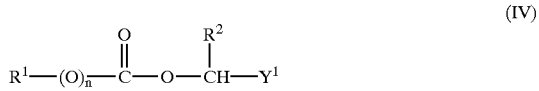

(IV)

(wherein $Y^1$ represents a halogen atom and other symbols are as defined above)[hereinafter referred to as a compound (IV), sometimes] and optionally subjecting the reaction product to anion exchange.

The halogen atom represented by $Y^1$ is preferably chlorine, bromine or iodine.

The reaction between the compound (III) and compound (IV) is usually carried out with or without a solvent which does not inhibit the reaction. As the solvent which does not inhibit the reaction, for example, ketones (e.g. acetone, 2-butanone, 2-pentanone, etc.), sulfoxides (e.g. dimethylsulfoxide, etc.), ethers (e.g. diethyl ether, tetrahydrofuran, dioxane, etc.), nitriles (e.g. acetonitrile, etc.), aromatic hydrocarbons (e.g. benzene, toluene, xylene, etc.), halogenated hydrocarbons (e.g. dichloromethane, chloroform, 1,2-dichloroethane, etc.), esters (e.g. ethyl acetate, etc.), amides (e.g. dimethylformamide, acetamide, dimethylacetamide, 1-methyl-2-pyrolidinone, etc.) and ureilenes (e.g. 1,3-dimethyl-2-imidazolidinone, etc.) are used. These solvents can be used alone or in combination thereof in an appropriate ratio.

The compound (IV) is used in an amount of about 1 to 100 equivalent, preferably about 1 to 5 equivalent, based on the compound (III).

The reaction temperature is not specifically limited, but is usually from about 0 to 150° C., preferably from about 20 to 120° C.

The reaction time is from several minutes to several hundreds hours (e.g. 5 minutes to 100 hours, etc.).

The compound thus obtained can be optionally converted into a compound (Ia) having a desired anion ($Y^-$) by anion exchange. The anion exchange can be carried out by treating with an anion type ion exchange resin, or an alkali metal (e.g. sodium, potassium, etc.) salt of an organic or inorganic acid described above for $Y^-$, in the presence of water, a mixed solvent of water and an organic solvent (e.g. acetone, acetonitorile, tetrahydrofuran, methanol, ethanol, etc.) or organic solvent.

The compound (I) thus obtained can be isolated and purified from the reaction mixture using a per se known means such as extraction, concentration, neutralization, filtration, recrystallization, column chromatography, thin layer chromatography, etc.

When the compound (I) used in the present invention has one or more asymmetric carbon atoms in the molecule, two or more stereoisomers exist, but those isomers can be separately prepared, if desired. For example, when the starting compounds (III) and (IV) have an asymmetric carbon atom in the molecule, a single isomer of the compound (Ia) can be obtained by carrying out above reaction using such single isomer. In addition, a single isomer of the reaction compound (Ia) can be obtained by carrying out above reaction using a single isomer of the starting compound (III). Also, when the product is a mixture of two or more kinds of isomers, the product can be separated by using a normal separation method, e.g. separation means such as various chromatographies and fractional recrystallization.

When the compound (III), which is the starting compound of Compound (Ia), is a per se known antifungal agent described above, the production method is known and methods of series of compounds which are useful as an antifungal agent are per se known, for example, the methods described in Japanese Patent Kokai Publication No. Hei 6-293740, Japanese Patent Kokai Publication No. Hei 8-104676 and WO-9625410A. In addition, the production method of the other starting compound (IV) is also known, and the compound can be produced by the method described in Synthesis, page 588 (1971) and Synthetic Communications, Vol. 25, page 2739 (1995), or a manner based on the method.

Compound (I) used in the present invention has an anti-fungal action with low toxicity and can thus be used as an anti-fungal agent. That is, the compound (I) can be used as a preventive or therapeutic agent against fungal infections in mammals (humans, domestic animals, domestic fowls, etc.) caused by various fungi such as microorganisms of the genus Candida (e.g., *Candida albicans, Candida utilis, Candida glabrata, Candida krusei, Candida tropicalis, Candida parapsilosis* etc.), microorganisms of the genus Trichosporon (e.g., *Trichosporon asahi* etc.), microorganisms of the genus Histoplasma (e.g., *Histoplasma capsulatum* etc.), microorganisms of the genus Aspergillosis (e.g., *Aspergillosis niger, Aspergillosis fumigatus, Aspergillosis flavus* etc.), microorganisms of the genus Penicillium (e.g., *Penicillium marneffei* etc.), microorganisms of the genus Cryptococcus (e.g., *Cryptococcus neoformans* etc.), microorganisms of the genus Trichophyton (e.g., *Trichophyton rubrum, Trichophyton mentagrophytes* etc.), microorganisms of the genus Microsporum (e.g., *Microsporum gypseum, Microsporum canis* etc.), microorganisms of the genus Malassezia (e.g., *Malassezia furfur* etc.), microorganisms of the genus Sporothrix (e.g., *Sporothrix schenckii* etc.), microorganisms of the genus Cladosporium (e.g., *Cladosporium carrionii* etc.), microorganisms of the genus Fonsecaea (e.g., *Fonsecaea compactur, Fonsecaea pedrosoi* etc.), microorganisms of the genus Phialophora (e.g., *Phialophora verrucosa* etc.), microorganisms of the genus Rhinocladiella (e.g., *Rhinocladiella aquaspersa* etc.), microorganisms of the genus Exophiala (e.g., *Exophiala jeanselmei* etc.), microorganisms of the genus Wangiella (e.g., *Wangiella dermatitidis* etc.), microorganisms of the genus Coccidioides (e.g., *Coccidioides immitis* etc.), microorganisms of the genus Epidermophyton (e.g., *Epidermophyton floccosum* etc.), microorganisms of the genus Paracoccidioides (e.g., *Paracoccidioides brasiliensis* etc.), microorganisms of the genus Blastomyces (e.g., *Blastomyces dermatitidis* etc.), and microorganisms of the genus Fusarium (e.g., *Fusarium dimerum* etc.), preferably against fungal infections by microorganisms of the *genera Candida*, Cryptococcus, Aspergillosis, and Coccidioides, particularly preferably against fungal infections by microorganisms of the genus Coccidioides. In particular, the compound (I) can be used in humans (immuno-compromised and non-immuno-compromised patients) including patients with AIDS, patients transplanted with organs and patients transplanted with bone marrow, in order to prevent or treat fungal infections [organ mycosis (deep-seated mycosis): hematomycosis, respiratory mycosis (e.g. pulmonary mycosis etc.), gastrointestinal mycosis, urinary tract mycosis, fungal osteomyelitis etc.; deep-seated dermatomycosis: sporotrichosis, chromomycosis; superficial dermatomycosis: trichophytosis (tinea corporis, coxarthrocace, tinea manus, athlete's foot tinea capitis, tinea kerion, tinea barbae etc.); discoloring desquamation by dermal fungus: hyperkeratosis; candidiasis (oral candidiasis, candidiasis cutis, candidiasis syncosis, chronic mucocutaneous candidiasis etc.); pityriasis versiclor; malassezia folliculitis; tinea unguium; keratomycosis; systemic mycosis; rare tropical mycosis; preferably against hematomycosis, respiratory mycosis, gastrointestinal mycosis, urinary tract mycosis, and fungal osteomyelitis etc.

Specifically, the compound (I) can be used in topical and/or systemic administration for prevention or treatment of e.g. mucous candidiasis (oral candidiasis, esophagus candidiasis, non-invasive bronchus candidiasis, thrush, angular stomatitis, vaginal candidiasis, penile candidiasis etc.), candidiasis cutis (candidiasis erosio interdigitalis, candidiasis interytigo, candidiasis periproctis, eczematoid candidiasis dermatis, candidiasis onychitis, candidiasis perionychia, candidiasis inflammation of external auditory meatus, dermatosis of candidiasis sepsis, universal superficial candidiasis, candidiasis granuloma, congential skin candidiasis, candidid, candidiasis sycosis, erythema myceticum infantile etc.), chronic mucosal skin candidiasis, disseminated candidiasis and visceral candidiasis [respiratory candidiasis (bronchial candidiasis, pulmonary candidiasis, pneumonia etc.), digestive system candidiasis, candidemia, candidemia, candidiasis endocarditis, candidiasis myocarditis, urinary system candidiasis, candidiasis of eyes, central nervous system candidiasis, articular and bony candidiasis, candidiasis peritonitis, hepatic candidiasis, intrauterine candidiasis' etc.], trichosporosis by microorganisms of the genus Trichosporon, acute lung histoplasmosis by microorganisms of the genus Histoplasma, chronic lung histoplasmosis and disseminated histoplasmosis, penicilliosis by microorganisms of the genus Penicillium, respiratory aspergillosis by microorganisms of the genus Aspergillosis [allergic aspergillosis, bronchial aspergillosis, aspergilloma, pulmonay aspergillosis (acute invasive aspergillosis, chronic necrotic pulmonay aspergillosis), aspergillosis empyema], disseminated aspergillosis, central nervous system aspergillosis, aspergillosis endocarditis, aspergillosis myocarditis, aspergillosis pericarditis, aspergilloma, aspergillosis of external auditory meatus, onychia of aspergillosis, aspergillosis inflammation of perionychium, aspergillosis corneitis, aspergillosis endophthalmitis, dermal aspergillosis, accessory sinus orbita aspergillosis; lung cryptococcosis by microorganisms of the genus Cryptococcus, central nervous system cryptococcosis, cryptococcosis meningitis, dermal and mucosal cryptococcosis, bony and articular cryptococcosis, lymph node cryptococcosis, systemic cryptococcosis and cryptococcosis of hematopoletic organs; ringworm of scalp, tinea captis, favus, Celsus' kerion, tinea barbae, spotted phlyctenula tinea, eczematous tinea, anfractuous tinea, athlete's foot, tinea unguium, trichophytid and tinea, granuloma trichophyticum etc. by microorganisms of the genera Trichophton, Microsporum and Epidermophyton; pityriasis versicolor, Malassezia folliculitis, folliculitis, intertrigo, seborrhea, dacryocystitis etc. by microorganisms of the genus Malassezia; sporotrichosis etc. by microorganisms of the genus Sporotrichum; Chromobacterium diseases (infections with black branched bacteria) by microorganisms of the genera Cladosporium, Fonsecae, Phialophora, Rhinocladiella, etc.; Chromobacterium diseases (infections with black hypha bacteria) by microorganisms of the genera Exophiala and Wangiella; coccidioidomycosis by microorganisms of the genus Coccidioides, para-coccidioidomycosis by the genera Paracoccidioides, blastomycosis by microorganisms of the genus Blastomyces; and Fusarium diseases by microorganisms of the genus Fusarium, and further the compound (I) can be used for prevention and treatment of atopic. dermatitis. Further, the composition of the present invention can contain two or more compounds (I), and may also contain other compounds having an anti-fungal action in addition to the compound (I).

The composition of the present invention comprising compound (I) and a saccharide can be produced by mixing compound (I) with the saccharide, or dissolving or suspending either or both of them in a suitable solvent such as water and then mixing both of them, followed by lyophilization thereof. The saccharide includes e.g. monosaccharides such as fructose and glucose, disaccharides such as maltose, cellobiose, gentiobiose, melibiose, lactose, turanose, sophorose, trehalose, isotrehalose, isosaccharose and white sugar, sugar alcohols such as mannitol, sorbitol, xylitol and inositol. In particular, maltose, lactose, trehalose, white sugar, mannitol and inositol are preferable, and inositol and trehalose are the most preferable.

Although the ratio of compound (I) to the saccharide mixed is not particularly limited, the amount of the saccharide is usually 0.001 to 1000 parts by weight, preferably 0.01 to 100 parts by weight, more preferably 0.1 to 20 parts by weight and most preferably 0.1 to 10 parts by weight relative to 1 part of compound (I).

The lyophilized product described in item (2) above can be produced in a known lyophilization method by lyophilizing an aqueous solution containing both compound (I) and the saccharide dissolved in a suitable solvent (e.g. a mixed solvent of water and alcohol). In the aqueous solution before lyophilization, the concentration of compound (I) is usually 0.01 mg/ml to 500 mg/ml, and the concentration of the saccharide is usually 0.01 mg/ml to 1,000 mg/ml. Lyophilization is conducted usually under the condition of 0.01 to 1.0 Torr, preferably 0.05 to 0.5 Torr, for 12 to 100 hours. Specifically, said aqueous solution is frozen at its eutectic point or less, and after the shelf temperature is gradually increased to a primary lyophilization temperature under vacuum in a drying chamber, the sample is subjected to primary lyophilization at the same temperature, and after the primary lyophilization is finished, the shelf temperature is gradually increased to a secondary drying temperature, and secondary lyophilization is carried out. The shelf temperature in the first and second lyophilization may be the same or different. The first lyophilization temperature is a temperature at which noticeable water or ice is eliminated, while the second lyophilization temperature is a temperature at which water which is hardly removable due to its strong bonding to the molecule can be completely eliminated. For example, the primary and secondary lyophilization temperatures for 4-acetoxymethyl-1-[(2R,3R)-2-(2,4-difluorophenyl)-2-hydroxy-3-[2-oxo-3-[4-(1H-tetrazol-1-yl)phenyl]-1-imidazolydinyl]butyl]-1H-1,2,4-triazolium chloride are about $-10°$ C. and about $45°$ C., respectively.

The lyophilized product thus obtained can maintain compound (I) stably for a long time and can be used as a pharmaceutical preparation for injection or as an agricultural anti-fungal agent.

Depending on use of the lyophilized product, other ingredients may be mixed therewith. For use thereof as e.g. a pharmaceutical preparation for injection, an agent (e.g. salts such as common salt) rendering the solution isotonic by regulating osmotic pressure, a pH-adjusting agent (e.g. citric acid buffer) etc. may be mixed with the aqueous solution before lyophilization, and before lyophilization, the aqueous solution containing both compound (I) and the saccharide may be filtered with 0.22 $\mu$m filter or treated to remove pyrogen to make the solution aseptic.

The lyophilized product for injection can be dissolved in injection water or intravenous infusion (e.g., physiological saline, glucose etc.) just before administration and used as an injection such as intravenous injection, subcutaneous injection, intramuscular injection or intravenous drip infusion, or as eye drops. This solution in injection water or in intravenous infusion is sufficiently stable. In this case, it is preferable that the concentration of compound (I) in the solution is e.g. about 0.01 mg/ml to 20 mg/ml, while the concentration of the salt is about 0.01 mg/ml to 400 mg/ml.

The dose of the composition of the present invention is varied depending on the state of infections, the administration route etc., but for oral administration into an adult patient (weight: 50 kg) for the purpose of treatment of candidiasis, the amount of compound (I) therein is about.0.01 to 100 mg/kg/day, preferably about 0.1 to 50 mg/kg/day and more preferably about 0.5 to 10 mg/kg, and for administration as an injection, the amount of compound (I) is about 0.01 to 100 mg/kg/day, preferably about 0.05 to 50 mg/kg/day and more preferably about 0.1 to 5 mg/kg/day.

When the composition of the present invention is used as an agricultural anti-fungal agent, the composition can be mixed with a suitable solid carrier (e.g., diluent, fillers) and used in the form of preparations such as powder, granules etc. These preparations can be prepared by any process known in the art. The amount of compound (I) used is about 250 to 150 g, preferably about 40 to 80 g per are of a paddy field in controlling e.g. rice blast disease.

Two or more compounds (I) may be used in combination, or single compound (I) may be used in combination with other agricultural anti-fungal compounds.

BEST MODE FOR CARRYING OUT THE INVENTION

The following Reference Examples, Examples, Preparation Examples and Experimental Examples illustrate the present invention in detail, but are not to be construed to limit the scope thereof.

$^1$H-NMR spectrum is measured by a Varian Gemini 200 (200 MHz) type spectrometer using tetramethylsilane as an internal standard, and all δ values were represented by ppm. The numerical value described in ( ) for the mixed solvent is a volume mixing ratio of each solvent. "%' s" are by weight unless otherwise stated. A ratio of the solvent in silica gel chromatography represents a volume ratio of solvents to be mixed.

The symbols in the Examples have the following meanings.

s: singlet, d: doublet, t: triplet, q: quartet, dd: double doublet, tt: triple triplet, m: multiplet, br: broad, J: coupling constant.

EXAMPLES

Reference Example 1

Tetrahydrofurfuryl alcohol (19.4 g) was dissolved in anhydrous ether (500 ml) and, after adding pyridine (15 g) under ice cooling, chloromethyl chloroformate (25 g) was added dropwise. After the reaction mixture was stirred at room temperature for 17 hours, the deposited pyridine hydrochloride was removed by filtration and the filtrate was washed with ether (50 ml×2). The washings and the filtrate were combined, washed with water (300 ml×2) and then dried over anhydrous magnesium sulfate. The solvent was distilled off under reduced pressure to obtain chloromethyl (2,3,4,5-tetrahydrofurfuryl) carbonate (33.9 g) as a colorless oily product.

$^1$H-NMR(CDCl$_3$) δ: 1.59–1.73(1H,m), 1.83–2.11(3H,m), 3.75–3.97(2H,m), 4.11–4.34 (3H,m), 5.74(2H,s)

Chloromethyl (2,3,4,5-tetrahydrofurfuryl)carbonate (3.4 g) and sodium iodide (10.46 g) were added to acetonitrile (70 ml), and then the mixture was heated with stirring at 60° for 90 minutes. After the reaction solution was cooled, the solvent was distilled off under reduced pressure, and the residue was partitioned between ether (70 ml) and a saturated sodium chloride aqueous solution (50 ml). The organic layer was washed with an aqueous 5% sodium thiosulfate solution (50 ml), water (50 ml) and a saturated sodium chloride aqueous solution (50 ml) successively, and then dried over anhydrous magnesium sulfate. The solvent was distilled off under reduced pressure to obtain iodomethyl (2,3,4,5-tetrahydrofurfuryl)carbonate (4.8 g) as a pale yellow oily product.

$^1$H-NMR(CDCl$_3$) δ: 1.54–1.73(1H,m), 1.84–2.11(3H,m), 3.73–3.96(2H,m), 4.10–4.32 (3H,m), 5.96(2H,s)

Reference Example 2

Glycerol formal (14 g) was dissolved in anhydrous ether (400 ml) and, after adding pyridine (15 g) at −10° C., a solution of chloromethyl chloroformate (25 g) in anhydrous ether (50 ml) was added dropwise over the period of 10 minutes. After the reaction solution was stirred at room temperature for 20 hours, the deposited pyridine hydrochloride was removed by filtration. The filtrate was washed with a saturated sodium chloride aqueous solution (400 ml×2), and then dried over anhydrous magnesium sulfate. The residue obtained by distilling off the solvent under reduced pressure was purified by subjecting it to silica gel chromatography (eluent: ethyl acetate/hexane=1/5→ethyl acetate/hexane=1/3) to obtain chloromethyl (1,3-dioxan-5-yl) carbonate (1.7 g) as a colorless oily product.

$^1$H-NMR(CDCl$_3$) δ: 4.05 (4 H, d, J 3.2 Hz), 4.67 (1 H, quintet, J=3.2 Hz), 4.82 (1 H, d, J=6.2 Hz), 4.95 (1H, d, J=6.2 Hz), 5.75 (2H, s).

The compound obtained above (1.7 g) and sodium iodide (5.1 g) were added to acetonitrile (40 ml), and then the mixture was stirred with heating at 60° C. for 2 hours. The residue obtained by distilling off the solvent of reaction mixture under reduced pressure was dissolved in ether (100 ml). The solution was washed with an aqueous 5% sodium thiosulfate solution (50 ml), water (50 ml) and a saturated sodium chloride aqueous solution (50 ml) successively, and then dried over magnesium sulfate. The solvent was distilled off under reduced pressure to obtain (1,3-dioxan-5-yl) iodomethyl carbonate (3.2 g) as a pale yellow oily product.

$^1$H-NMR(CDCl$_3$) d :4.04 (4H, d, J=3.0 Hz), 4.66 (1H, quintet, J=3.0 Hz), 4.81 (1H, d, J=6.2 Hz), 4.95 (1H, d, J=6.2 Hz), 5.97 (2H, s).

Reference Example 3

(R)-Glycerol acetonide (10 g) was dissolved in anhydrous ether (200 ml) and, after adding pyridine (6.6 g) at −10° C., a solution of chloromethyl chloroformate (10.7 g) in anhydrous ether (20 ml) was added dropwise over the period of 10 minutes. After the reaction mixture was stirred at room temperature for 20 hours, the deposited pyridine hydrochloride was removed by filtration. The filtrate was washed with a saturated sodium chloride aqueous solution (200 ml×2), and then dried over anhydrous magnesium sulfate. The residue obtained by distilling off the solvent under reduced pressure was purified by subjecting it to silica gel chromatography (eluent: hexane→ethyl acetate/hexane=1/5 →ethyl acetate/hexane=3/5) to obtain chloromethyl [(4S)-2,2-dimethyl-1,3-dioxolan-4-yl]methyl carbonate (17 g) as a colorless oily product.

$^1$H-NMR(CDCl$_3$) δ: 1.37 (3H, s), 1.44 (3H, s), 3.80 (1H, dd, J=8.8, 5.8 Hz), 4.07–4.42 (4H, m), 5.74 (2H, s).

The compound obtained above (2 g) and sodium iodide (5.3 g) were added to acetonitrile (40 ml), and then the mixture was stirred with heating at 60° C. for 2 hours. The residue obtained by distilling off the solvent of reaction solution under reduced pressure was dissolved in ether (50 ml). The solution was washed with an aqueous 5% sodium thiosulfate solution (50 ml), water (50 ml), and a saturated sodium chloride aqueous solution (50 ml) successively, and then dried over anhydrous magnesium sulfate. The solvent was distilled off under reduced pressure to obtain [(4S)-2,2-dimethyl-1,3-dioxolan-4-yl]methyl iodomethyl carbonate (2.1 g) as a pale yellow oily product.

$^1$H-NMR(CDCl$_3$) δ: 1.37 (3H, s), 1.44 (3H, s), 3.79 (1H, dd, J=8.0, 5.0 Hz), 4.06–4.41 (4H, m), 5.96 (2H, s).

Reference Example 4

To a solution of benzyl 4-hydroxybutanoate (synthesized by the procedure described in Weber et al., J. Med. Chem, 1991, 34, 2692–2701, 5.0 g) in diethyl ether (100 ml), pyridine (2.3 ml) was added under a nitrogen atmosphere, and chloromethyl chloroformate (3.7 g) was added dropwise at −10 ° C. The reaction mixture was stirred at room temperature for 20 hours. The reaction mixture was filtered with glass filter and then the filtrate was washed with water and a saturated sodium chloride aqueous solution successively. The organic layer was dried over magnesium sulfate, and then the solvent was distilled off under reduced pressure, and thus the residue was subjected to silica gel column chromatography and eluted with acetone/hexane (1:1 v/v) to obtain chloromethyl (3-benzyloxycarbonylpropyl) carbonate (7.25 g) as a colorless oily product.

$^1$H-NMR(CDCl$_3$) d : 2.02–2.12 (2H, m), 2.49 (2H, t, J=7 Hz), 4.28 (2H, t, J=6 Hz), 5.13 (2H, s), 5.71 (2H, s), 7.36 (5H, s).

To a solution of the compound obtained above (2.5 g) in acetonitrile (67 ml) was added sodium iodide (5.2 g) under a nitrogen atmosphere. The mixture was stirred at 60° C. for 8.5 hours. The solvent was distilled off under reduced pressure, and the residue was dissolved in diethyl ether (100 ml). The solution was washed with an aqueous 5% sodium thiosulfate solution, water, and a saturated sodium chloride aqueous solution successively. The organic layer was dried over sodium sulfate, and then concentrated under reduced pressure to obtain (3-benzyloxycarbonylpropyl) iodomethyl carbonate (2.98 g) as a pale yellow oily product.

$^1$H-NMR(CDCl$_3$) d: 2.01–2.08 (2H, m), 2.49 (2H, t, J=7 Hz), 4.28 (2H, t, J=6 Hz), 5.14 (2H, s), 5.94 (2H, s), 7.36 (5H, s).

Reference Example 5

To the mixture of ethyl (S)-lactate (23.6 g), pyridine (15.8 g) and diethyl ether (400 ml) was added dropwise a solution of chloromethyl chloroformate (25.6 g) in diethyl ether (100 ml) under ice cooling over the period of 40 minutes. After stirring at room temperature for 14 hours, the resulting solid was removed off by filtration. The filtrate was concentrated under reduced pressure and the residue was dissolved in ethyl acetate (250 ml). The solution was washed with water (150 ml×2) and a saturated sodium chloride aqueous solution (150 ml). After drying over anhydrous magnesium sulfate, the solvent was distilled off under reduced pressure to obtain chloromethyl [(1S)-1-(ethoxycarbonyl)ethyl] carbonate (38.5 g) as a colorless liquid.

$^1$H-NMR(CDCl$_3$) δ: 1.30(3H,t,J=7.2 Hz), 1.57(3H,d,J=7.0 Hz), 4.25(2H,q,J=7.2 Hz), 5.07(1H,q,J=7.0 Hz), 5.71 (1H,d,J=6.4 Hz), 5.80(1H,d,J=6.4 Hz).

Reference Example 6

To a mixture of benzyl (S)-lactate (30.6 g), pyridine (13.4 g) and diethyl ether (300 ml), a solution of chloromethyl chloroformate (21.9 g) in diethyl ether (100 ml) was added dropwise under ice cooling over the period of 30 minutes. After stirring at room temperature for 5 hours, the resulting solid was removed off by filtration. The filtrate was concentrated under reduced pressure and the residue was dissolved in ethyl acetate (200 ml). The solution was washed with water (100 ml×2) and a saturated sodium chloride aqueous solution (100 ml). After drying over anhydrous magnesium sulfate, the solvent was distilled off under reduced pressure to obtain [(1S)-1-(benzyloxycarbonyl)ethyl]chloromethyl carbonate (45.0 g) as a colorless liquid.

$^1$H-NMR(CDCl$_3$) δ: 1.57(3H,d,J=7 Hz), 5.07–5.28(3H, m), 5.69(1H,d,J=6 Hz), 5.78(1H,d,J=6 Hz), 7.36(5H,s).

[(1S)-1-(benzyloxycarbonyl)ethyl]chloromethyl carbonate (2.7 g) was dissolved in acetonitrile (4 ml) and sodium iodide (6.0 g) was added. The mixture was stirred at 60 for 2 hours under an argon atmosphere. After the reaction mixture was concentrated under reduced pressure, diethyl ether (100 ml) and water (100 ml) were added to the residue. The diethyl ether layer was separated and washed with an aqueous 5% sodium thiosulfate solution (80 ml), water (80 ml), and a saturated sodium chloride aqueous solution (80 ml) successively. After drying over anhydrous magnesium sulfate, the solvent was distilled off under reduced pressure to obtain [(1S)-1-(benzyloxycarbonyl)ethyl]iodomethyl carbonate (3.3 g) as a colorless liquid.

$^1$H-NMR(CDCl$_3$) δ: 1.56(3H,d,J=7 Hz), 5.07–5.29(3H, m), 5.93(1H,d,J=5 Hz), 5.98(1H,d,J=5 Hz), 7.37(5H,s).

Reference Example 7

To a solution of 3-(benzyloxy)propanol (synthesized by a procedure described in Wei et al., J. Org. Chem, 54, 5768–5774 (1989):15.1 g) and pyridine (7.18 g) in diethyl ether (150 ml), a solution of chloromethyl chloroformate (11.7 g) in diethyl ether (50 ml) was added dropwise under ice cooling over the period of 20 minutes. After stirring at room temperature for 15 hours, the resulting solid was removed off by filtration and washed with ethyl acetate (100 ml). The filtrate and the washings were combined, and washed with water (100 ml×2) and a saturated sodium chloride aqueous solution (50 ml). After drying the solution over anhydrous magnesium sulfate, the solvent was distilled off under reduced pressure. The residue was purified by subjecting it to silica gel chromatography (silica gel 200 g, eluent: ethyl acetate-hexane=1:4) to obtain [3-(benzyloxy)propyl]chloromethyl carbonate (21.0 g) as a colorless liquid.

$^1$H-NMR(CDCl$_3$) δ: 2.01(2H,quintet,J=6.2 Hz), 3.57(2H, t,J=6.0 Hz), 4.36(2H,t,J=6.4 Hz), 4.51(2H,s), 5.71(2H,s), 7.33(5H,s).

[3-(Benzyloxy)propyl]chloromethyl carbonate (2.0 g) was dissolved in acetonitrile (3 ml), and sodium iodide (4.6 g) was added. The mixture was stirred under a nitrogen atmosphere at 60° C. for 2 hours. The reaction mixture was poured into water (100 ml) and extracted with ethyl acetate (100 ml). The ethyl acetate layer was washed with an aqueous 5% sodium thiosulfate solution (50 ml×2), water (50 ml×2), and a saturated sodium chloride aqueous solution (50 ml). After drying over anhydrous magnesium sulfate, the solvent was distilled off under reduced pressure to obtain [3-(benzyloxy)propyl]iodomethyl carbonate (2.5 g) as a pale yellow liquid.

$^1$H-NMR(CDCl$_3$) 67 : 2.00(2H,quintet,J=6.2 Hz), 3.57 (2H,t,J=6.0 Hz), 4.36(2H,t,J=6.4 Hz), 4.51(2H,s), 5.94(2H, s), 7.34(5H,s).

Reference Example 8

To a mixture of 2-acetylaminoethanol (20.0 g), pyridine (15.3 g) and tetrahydrofuran (100 ml), a solution of chloromethyl chloroformate (25.2 g) in tetrahydrofuran (50 ml)

was added dropwise under ice cooling over the period of 30 minutes. After stirring at room temperature for 16 hours, the resulting solid was removed off by filtration and washed with tetrahydrofuran (30 ml). The filtrate and the washing were combined, and concentrated under reduced pressure. To the residue, ethyl acetate (300 ml) and water (100 ml) were added and the organic layer was separated. The aqueous layer was extracted twice with a mixture of ethyl acetate (150 ml) and tetrahydrofuran (50 ml). The organic layers were combined, washed with a saturated sodium chloride aqueous solution (100 ml), and dried over anhydrous magnesium sulfate. The solvent was distilled off under reduced pressure. The residue was purified by subjecting it to silica gel chromatography (silica gel 240 g, eluent: ethyl acetate-hexane=1:1→ethyl acetate) to obtain [2-(acetylamino)ethyl] chloromethyl carbonate (32.4 g) as a colorless oil.

$^1$H-NMR(CDCl$_3$) δ: 2.01(3H,s), 3.58(2H,q,J=6 Hz), 4.32 (2H,t,J=6 Hz), 5.75(2H,s), 5.87(1H,br).

[2-(acetylamino)ethyl]chloromethyl carbonate (5.0 g) was dissolved in acetonitrile (15 ml), and sodium iodide (15.0 g) was added. The mixture was stirred at 60° C. for 2 hours under an argon atmosphere. The reaction mixture was poured into ice water (200 ml) and extracted with ethyl acetate (200 ml). The extract was washed with an aqueous 5% sodium thiosulfate solution (100 ml×2), water (100 ml×2) and a saturated sodium chloride aqueous solution (50 ml) successively. After drying over anhydrous magnesium sulfate, the solvent was distilled off under reduced pressure to obtain [2-(acetylamino)ethyl]iodomethyl carbonate (3.5 g) as a yellow oil.

$^1$H-NMR(CDCl$_3$) δ: 2.00(3H,s), 3.54(2H,q,J=6 Hz), 4.28 (2H,t,J=6 Hz), 5.93(2H,s), 6.12(1H,br).

Reference Example 9

To a mixture of 3-(methoxy)propanol (6.0 g), pyridine (5.3 g) and diethyl ether (50 ml), a solution of chloromethyl chloroformate (8.6 g) in diethyl ether (10 ml) was added dropwise under ice cooling over the period of 15 minutes. After stirring at room temperature for 16 hours, water (100 ml) and ethyl acetate (100 ml) were added, and the organic layer was separated. The organic layer was washed with water (100 ml) and a saturated sodium chloride aqueous solution (50 ml), and after drying over anhydrous magnesium sulfate, the solvent was distilled off under reduced pressure. The residue was purified by subjecting it to silica gel chromatography (silica gel 70 g, eluent: ethyl acetate-hexane=1:2) to obtain chloromethyl [3-(methoxy)propyl] carbonate (11.0 g) as a colorless liquid.

$^1$H-NMR(CDCl$_3$) δ: 1.97(2H,quintet,J=6.2 Hz), 3.34(3H, s), 3.47(2H,t,J=6.2 Hz), 4.33(2H,t,J=6.2 Hz), 5.74(2H,s).

Chloromethyl [3-(methoxy)propyl]carbonate (3.7 g) was dissolved in acetonitrile (12 ml), and sodium iodide (12.0 g) was added. The mixture was stirred at 55° C. for 4 hours under an argon atmosphere. The reaction mixture was poured into water (100 ml) and extracted with ethyl acetate (100 ml). The ethyl acetate layer was washed with an aqueous 5% sodium thiosulfate solution (50 ml×2), water (50 ml) and a saturated sodium chloride aqueous solution (50 ml). After drying over anhydrous magnesium sulfate, the solvent was distilled off under reduced pressure to obtain iodomethyl [3-(methoxy)propyl]carbonate (5.0 g) as a pale yellow liquid.

$^1$H-NMR(CDCl$_3$) δ: 1.96(2H,quintet,J=6.2 Hz), 3.35(3H, s), 3.47(2H,t,J=6.2 Hz), 4.33(2H,t,J=6.2 Hz), 5.96(2H,s).

Reference Example 10

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.25 g) and chloromethyl pivalate (3.0 g) was stirred for 24 hours at 100° C. After having been cooled, the mixture was diluted with diethyl ether(5 ml), and the resulting powder was collected by filtration. The powder was purified by octadecyl silica (hereinafter briefly referred to as ODS) column chromatography (eluent: methanol/water=3/2) to give 1-[(2R, 3R)-2-(2,4-difluorophenyl)-2-hydroxy-3-[2-oxo-3-[4-(1H-1,2,3-triazol-1-yl)phenyl]-1-imidazolidinyl]butyl]-4-[(2,2-dimethylpropanoyloxy)methyl]-1H-1,2,4-triazolium chloride (Compound 1, 0.10 g) as a white powder.

$^1$H-NMR(d$_6$-DSMO) δ: 0.97(3H,d,J=7 Hz), 1.13(9H,s), 3.61–4.10(4H,m), 4.65–4.75(1H,m), 4.89(1H,d,J=14 Hz), 5.13(1H,d,J=14 Hz), 6.17(2H,s), 6.74(1H,s), 6.91–7.01(1H, m), 7.21–7.36(2H,m), 7.82–7.93(4H,m), 7.95(1H,d,J=1.2 Hz),. 8.79(1H,d,J=1.2 Hz), 9.11(1H,s), 10.53(1H,s).

Reference Example 11

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.5 g) and chloromethyl pivalate (3.1 g) was stirred for 2 hours at 100° C. After having been cooled, the mixture was diluted with diisopropyl ether (10 ml), and the resulting powder was collected by filtration. The powder was subjected to silica gel flush chromatography (eluent: ethyl acetate→acetone→acetone/ethanol=10/1→acetone/ethanol=5/1) to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(2,2-dimethylpropanoyloxy) methyl]-1H-1,2,4-triazolium chloride (Compound 1, 0.34 g) as a white powder.

Reference Example 12

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.5 g) and chloromethyl pivalate (4.7 g) was stirred for 5 hours at 100° C. After having been cooled, the mixture was diluted with diisopropyl ether (10 ml), and the resulting powder was collected by filtration. The resulting powder was subjected to CHP-20P column chromatography (eluent: water→5% aqueous solution of acetonitrile→30% aqueous solution of acetonitrile→5aqueous solution of tetrahydrofuran→10% aqueous solution of tetrahydrofuran→20% aqueous solution of tetrahydrofuran) to give 1-[(2R,3R)-2-(2,4-difluorophenyl)-2-hydroxy-3-[2-oxo-3-[4-[3-(2,2-dimethylpropanoyloxy)methyl-1(1H)-1,2,3-triazolio]phenyl]-1-imidazolidinyl]butyl]-4-[(2,2-dimethylpropanoyloxy)methyl]-1H-1,2,4-triazolium dichloride (Compound 8, 134 mg) as a white powder and Compound 1 (141 mg) as a white powder.

Compound 8: $^1$H-NMR(d$_6$-DSMO) 67 : 0.97(3H,d,J=6.8 Hz), 1.13(9H,s), 1.21(9H,s), 3.63–3.66(1H,m), 3.98–4.15 (3H,m), 4.62–4.78(1H,m), 4.88(1H,d,J=14 Hz), 5.23(1H,d, J=14 Hz), 6.17(2H,s), 6.64(2H,s), 6.88(1H,s), 6.90–7.00 (1H,m), 7.21–7.36(2H,m), 7.98(2H,d,J=9.8 Hz), 8.05(2H,d, J=9.8 Hz), 9.10(1H,s), 9.34(1H,d,J=2.0 Hz), 9.68(1H,d,J= 2.0 Hz), 10.64(1H,s).

Reference Example 13

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.48 g) and acetone (10 ml) was added chloromethyl pivalate (2.9 ml), and the mixture was stirred under reflux. After 88 hours, chloromethyl pivalate (1.45 ml) was added to the mixture. The mixture was further stirred for 14 hours under reflux. The reaction mixture was concentrated under reduced pressure. To the residue was added diethyl ether (8 ml), and the resulting powder was collected by filtration. The powder was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,2-dimethylpropanoyloxy)methyl]-1H-1,2,4-triazolium chloride (Compound 2, 0.25 g) as a white powder.

$^1$-H-NMR($d_6$-DSMO) δ: 0.97(3H,d,J=7 Hz), 1.13(9H,s), 3.61–4.09(4H,m), 4.65–4.75(1H,m), 4.88(1H,d,J=14 Hz), 5.14(1H,d,J=14 Hz), 6.16(2H,s), 6.75(1H,s), 6.91–7.01(1H,m), 7.21–7.37(2H,m), 7.90(4H,s), 9.10(1H,s), 10.07(1H,s), 10.53(1H,s).

Reference Example 14

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(0.5 g), chloromethyl pivalate (15.7 g) and acetonitrile (2.4 g) was stirred for 6.5 hours at 100° C. After having been cooled, the mixture was diluted with diisopropyl ether (10 ml), and the resulting powder was collected by filtration. The powder was subjected to silica gel column chromatography (eluent: ethyl acetate→acetone→acetone/ethanol=10/1→acetone/ethanol=5/1) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,2-dimethylpropanoyloxy)methyl]-1H-1,2,4-triazolium chloride(Compound 2, 0.32 g) as a white powder. The above Compound 2 (0.4 g) was crystallized from ethyl acetate (20 ml) to give white crystals (0.3 g) of Compound -2.

Melting point: 196–197° C. (decomposition)

Elemental Analysis: $C_{28}H_{32}ClF_2N_9O_4$

Calcd. (%): C, 53.21; H, 5.10; N, 19.94

Found (%): C, 53.17; H, 5.15; N, 19.76

Reference Example 15

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.30 g) and chloromethyl acetate (1.35 g) was stirred for 24 hours at 100° C. The reaction mixture was concentrated under reduced pressure. The residue was subjected to ODS column chromatography (eluent: methanol/water=3/2) to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium chloride (Compound 3, 45 mg) as a white powder.

$^1$H-NMR($d_6$-DSMO) δ: 0.97(3H,d,J=7 Hz), 2.08(3H,s), 3.61–4.08(4H,m), 4.65–4.75(1H,m), 4.86(1H,d,J=14 Hz), 5.11(1H,d,J=14 Hz), 6.07–6.20(2H,m), 6.69(1H,s), 6.96–7.05(1H,m), 7.25–7.36(2H,m), 7.82–7.95(5H,m), 8.78(1H,s), 9.06(1H,s), 10.46(1H,s).

Reference Example 16

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.63 g) and acetonitrile (20 ml) was added chloromethyl isobutylate (1.71 g), and the mixture was stirred for 130 hours under reflux. The reaction mixture was concentrated under reduced pressure. To the residue was added diisopropyl ether (10 ml), and the resulting powder was collected by filtration. The powder was subjected to ODS column chromatography (eluent: methanol/water=3/2), and the eluate was concentrated in vacuo. The residue was dissolved in water (20 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(2-methylpropanoyloxy)methyl]- 1H-1,2,4-triazolium chloride (Compound 4, 0.335 g) as a white powder.

$^1$H-NMR($d_6$-DSMO) δ: 0.97(3H,d,J=7 Hz), 1.07(6H,d, J=7 Hz), 2.59(1H,quintet, J=7 Hz), 3.60–4.09(4H,m), 4.65–4.75(1H,m), 4.87(1H,d,J=14 Hz), 5.10(1H,d, J=14 Hz), 6.10–6.22(2H,m), 6.69(1H,s), 6.93–7.02(1H,m), 7.23–7.35(2H,m), 7.82–7.93(4H,m), 7.95(1H,s), 8.78(1H,s), 9.08(1H,s), 10.48(1H,s).

Reference Example 17

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.50 g) and acetone (20 ml) was added chloromethyl isobutylate (1.37 g), and the mixture was stirred for 50 hours under reflux. The reaction mixture was concentrated under reduced pressure. To the residue was added diisopropyl ether (10 ml), and the resulting powder was collected by filtration. The powder was subjected to ODS column chromatography (eluent: methanol/water=3/2). The eluate was concentrated in vacuo. The residue was dissolved in water (20 ml). The solution was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2-methylpropanoyloxy)methyl]-1H-1,2,4-triazolium chloride (Compound 5, 0.15 g) as a white powder.

$^1$H-NMR($d_6$-DSMO) δ: 0.97(3H,d,J=7 Hz), 1.07(6H,d, J=7 Hz), 2.59(1H,quintet, J=7 Hz), 3.61–4.08(4H,m), 4.65–4.75(1H,m), 4.87(1H,d,J=14 Hz), 5.11(1H,d, J=14 Hz), 6.14–6.22(2H,m), 6.69(1H,s), 6.92–7.03(1H,m), 7.22–7.37(2H,m), 7.90(4H,s), 9.09(1H,s), 10.08(1H,s), 10.48(1H,s).

The product (50 mg) was crystallized from saturated aqueous solution of sodium chloride (1 ml) to give white powdery crystals of Compound 5. (41 mg).

Melting point: 217–219° C. (decomposition)

Elemental Analysis: $C_{27}H_{30}ClF_2N_9O_4 \cdot 0.5H_2O$

Calcd (%): C, 51.72; H, 4.98; N, 20.10

Found (%): C, 51.79; H, 4.83; N, 20.04

Reference Example 18

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (100 mg) and 1-chloroethyl ethyl carbonate (1.0 g) was added acetonitrile (0.5 ml), and the mixture was stirred for 60 hours at 85° C. After having been cooled, the mixture was diluted with diisopropyl ether (4 ml), and the resulting powder was collected by filtration. The powder was subjected to ODS column chromatography (eluent: methanol/water=3/2). The eluate was concentrated in vacuo. The residue was dissolved in water (10 ml) and lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[1-(ethoxycarbonyloxy)ethyl]-1H-1,2,4-triazolium chloride (Compound 6, 36 mg) as a white powder.

$^1$H-NMR($d_6$-DSMO) δ: 0.97(3H,d,J=7 Hz), 1.21,1.22 (3H,t,J=7 Hz), 1.80(3H,d, J=6 Hz), 3.61–4.25(6H,m), 4.63–5.09(3H,m), 6.67–6.83(2H,m), 6.94–7.03(1H,m), 7.21–7.37(2H,m), 7.82–8.05(5H,m), 8.79(1H,s), 9.22(0.5H, s), 9.27(0.5H,s), 10.70(0.5H,s), 10.80(0.5H,s).

Reference Example 19

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.61 g) and 1-chloroethyl ethyl carbonate (3.7 g) was added acetonitrile (1 ml), and the mixture was stirred for 38 hours at 95° C. The reaction mixture was concentrated under reduced pressure. To the residue was added diisopropyl ether (10 ml), and the resulting powder was collected by filtration. The powder was subjected to ODS column chromatography (eluent: methanol/water=3/2). The eluate was concentrated in vacuo. The residue was dissolved in water (10 ml), and lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[-1-(ethoxy-carbonyloxy)ethyl]-1H-1,2,4-triazolium chloride (Compound 7,90 mg) as a white powder.

$^1$H-NMR(d$_6$-DSMO) δ: 0.97(3H,d,J=7 Hz), 1.21,1.22 (3H,t,J=7 Hz), 1.79,1.80(3H, d,J=6 Hz), 3.62–4.23(6H,m), 4.65–5.10(3H,m), 6.69–6.82(2H,m), 6.94–7.04(1H,m), 7.26–7.38(2H,m), 7.90(4H,s), 9.23(0.5H,s), 9.27(0.5H,s), 10.08(1H,s), 10.72(0.5H,s), 10.82(0.5H,s).

Reference Example 20

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(o.5 g), chloromethyl isopropyl carbonate (3.2 g) and acetonitrile (1 ml) was stirred for 25 hours at 100° C. After having been cooled, the mixture was diluted with diisopropyl ether (10 ml), and the resulting powder was collected by filtration and subjected to the silica gel column chromatography (eluent: ethyl acetate→acetone→acetone/ethanol=10/1→acetone/ethanol=5/1). Solvent was distilled off under reduced pressure, and residue was subjected to crystallization from ethyl acetate. The crystals were dissolved in water (10 ml). The aqueous solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(isopropoxycarbonyloxy)methyl]-1H-1,2,4-triazolium chloride (Compound 9, 0.18 g) as a white powder.

$^1$H-NMR(d$_6$-DSMO) δ: 0.98(3H,d,J=7 Hz), 1.24(6H,d,J=6.4 Hz), 3.52.–3.67(1H,m), 3.93–4.00(3H,m), 4.69(1H,q, J=7 Hz), 4.80(1H,quintet,J=6.4 Hz), 4.88(1H,d, J=13.8 Hz), 5.05(1H,d,J=13.8 Hz), 6.12(1H,d,J=10.8 Hz), 6.20(1H,d,J=10.8 Hz), 6.98–7.03(1H,m), 7.23–7.36(2H,m), 7.84(2H,d, J=8 Hz), 7.91(2H,d,J=8 Hz), 7.94 (1H,d,J=1H,z), 8.77(1H, d,J=1H,z), 9.10(1H,s), 10.38(1H,s). The lyophilized product of compound 9 above obtained (0.05 g) was recrystallized from acetonitrile (3 ml) to give white crystals (0.01 g) of Compound 9.

Elemental Analysis: C$_{28}$H$_{31}$ClF$_2$N$_8$O$_5$.H$_2$O
Calcd.: (%): C, 51.65; H, 5.11; N, 17.21
Found: (%): C, 51.64; H, 4.68; N, 17.06

Reference Example 21

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.5 g) and acetonitrile (10 ml) was added bromomethyl acetate (0.1 ml), and the mixture was stirred for 24 hours at 50° C. The reaction mixture was purified by silica gel flush chromatography (silica gel 25 g, eluent: ethyl acetate→acetone→acetone/ethanol=10/1). The residue purified was crystallized from ethanol to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium bromide (Compound 10, 0.135 g) as colorless crystals.

$^1$H-NMR(d$_6$-DMSO) δ: 0.98(3H,d,J=7 Hz), 2.08(3H,s), 3.62–4.08(4H,m), 4.66–4.75 (1H,m), 4.87(1H,d,J=14 Hz), 4.99(1H,d,J=14 Hz), 6.07–6.21(2H,m), 6.34(1H,s), 6.96–7.07(1H,m), 7.24–7.35(2H,m), 7.83–7.94(5H,m), 8.80 (1H,s), 9.09(1H,s), 10.24(1H,s)

Reference Example 22

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g) and acetonitrile (10 ml) was added bromomethyl acetate (0.2 ml), and the mixture was stirred for 16 hours at 50° C.

The reaction mixture was purified by silica gel flush chromatography (silica gel: 25 g, eluent: ethyl acetate→acetone→acetone/ethanol=10/1). The residue purified was crystallized from ethanol to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium bromide (Compound 11, 0.39 g) as colorless crystals.

$^1$H-NMR(d$_6$-DMSO) δ: 0.99(3H,d,J=7 Hz), 2.09(3H,s), 3.64–4.08(4H,m), 4.68–4.72 (1H,m), 4.86(1H,d,J=14 Hz), 5.01(1H,d,J=14 Hz), 6.07–6.21(2H,m), 6.35 (1H,s), 7.00–7.09(1H,m), 7.28–7.38(2H,m), 7.91(4H,s), 9.10(1H,s), 10.08 (1H,s), 10.28(1H,s)

Reference Example 23

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g) and acetonitrile (10 ml) was added iodomethyl (2,3,4,5-tetrahydrofurfuryl) carbonate (0.594 g), and the mixture was stirred for 15 hours at 50° C. The reaction mixture was subjected to silica gel flush chromatography (eluent: ethyl acetate→acetone→acetone/ethanol=10/1), and the fraction containing the desired compound was concentrated under reduced pressure. The residue was subjected to ODS column chromatography (eluent: methanol/water=3/2). The fraction containing the desired compound was concentrated and the residue was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,3,4,5-tetrahydrofurfuryl)oxycarbonyloxymethyl]-1H-1,2,4-triazolium iodide (Compound 30, 0.4 g) as a colorless powder. The product was dissolved in water (15 ml), and the solution was subjected to ion-exchange resin [Dowex 1×8 (Cl$^-$ type)]. The fraction containing the desired compound was concentrated under reduced pressure, and lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,3,4,5-tetrahydrofurfuryl)oxycarbonyloxymethyl]-1H-1,2,4-triazolium chloride (Compound 21, 0.24 g) as a colorless powder.

$^1$H-NMR(d$_6$-DMSO) δ: 0.97(3H,d,J=7 Hz), 1.52–1.99 (4H,m), 3.61–4.17(9H,m), 4.67–4.82(1H,m), 4.86(1H,d,J=14 Hz), 5.10(1H,d,J=14 Hz), 6.11–6.25(2H,m), 6.65(1H,s), 6.69–7.06(1H,m), 7.28–7.39(2H,m), 7.90(4H,s), 9.10(1H,s), 10.08(1H,s), 10.47(1H,s)

Reference Example 24

4-Acetoxymethyl-1-[(2R,3R)-2-(2,4-difluorophenyl)-2-hydroxy-3-[2-oxo-3-[4-(1H-tetrazol-1-yl)phenyl]-1- imidazolidinyl]butyl]-1H-1,2,4-triazolium bromide (Compound 11, 0.81 g) was subjected to ion-exchange resin [Dowex 1×8 (Cl⁻ type)] (eluent: water). The eluate was lyophilized to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 0.61 g) as a white powder.

$^1$H-NMR (d$_6$-DMSO) δ: 0.97 (3H, d, J=7.4 Hz), 2.08 (3H, s), 3.62–3.66 (1H, m), 3.90–4.07 (3H, m), 4.69 (1H, q, J==7.4 Hz), 4.85 (1H, d, J=14.6 Hz), 5.04 (1H, d, J =14.6 Hz), 6.09 (1H, d, J=11H,z), 6.16 (1H, d, J=11H,z), 6.55 (1H, s), 6.98–7.06 (1H, m), 7.23–7.38 (2H, m), 7.90 (4H, s), 9.06 (1H, s), 10.06 (1H, s), 10.34 (1H, s).

The lyophilized product (1.1 g) of Compound 12 obtained above was recrystallized from ethanol (20 ml) to give Compound 12 as white crystals (1 g).

Elemental Analysis: $C_{25}H_{26}ClF_2N_9O_4$

Calcd.: (%): C; 50.89, H; 4.44, N; 21.37, Cl; 6.01,

Found: (%): C; 50.61, H; 4.38, N; 21.24, Cl; 5.80.

The crystals (0.63 g) of Compound 12 was dissolved in water (10 ml), and the solution was allowed to stand overnight at 0° C. to give the hydrate (0.61 g) of Compound 12 as white crystals.

Elemental Analysis: $C_{25}H_{26}ClF_2N_9O_4.H_2O$

Calcd.: (%): C; 49.39, H; 4.64, N; 20.73,

Found: (%): C; 49.56, H; 4.64, N; 20.85.

Reference Example 25

4-Acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium bromide (Compound 11, 0.5 g) was dissolved in tetrahydrofuran (100 ml). To the solution was added saturated aqueous solution (100 ml) of sodium chloride. The mixture was shaken and the organic layer was separated. The shaking with sodium chloride solution followed by separation of the organic layer was repeated five times. The organic layer was dried over magnesium sulfate and the solvent was distilled off. The residue was recrystallized from ethanol (5 ml) to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 0.28 g) as white crystals. The physicochemical properties of this product were identical with those of the crystals of Compound 12 obtained by crystallization from ethanol in Reference Example 24.

Reference Example 26

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1 g), iodomethyl acetate (0.8 g) and acetonitrile (15 ml) was stirred for 15 hours at 50–55° C. The solvent was distilled off, and the residue was dissolved in tetrahydrofuran (100 ml). The solution was washed once with saturated aqueous solution (100 ml) of sodium chloride containing a small amount of sodium thiosulfate, followed by washing for four times with saturated aqueous solution (100 ml) of sodium chloride. The organic layer was dried over magnesium sulfate, and the solvent was distilled off under reduced pressure. The residue was subjected to silica gel chromatography (eluent: ethyl acetate→acetone→acetone/ethanol=10/1→acetone/ethanol=5/1). The solvent was distilled off, and the residue was crystallized from ethanol (10 ml) to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 0.44 g) as white crystals. The physicochemical properties of this product were identical with those of the crystals of Compound 12 obtained by crystallization from ethanol in Reference Example 24.

Reference Example 27

4-Acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium bromide (Compound 10, 0.03 g) was subjected to ion-exchange resin [Dowex 1×8 (Cl⁻ type)] (eluent: water). The eluate was lyophilized to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium chloride (Compound 3, 0.02 g) as a white powder.

Elemental Analysis: $C_{26}H_{27}ClF_2N_8O_4.2H_2O$

Calcd.: C; 49.96, H; 5.00, N; 17.93, Cl; 5.67,

Found : C; 49.98, H; 4.57, N; 17.95, Cl; 6.04.

Reference Example 28

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g), chloromethyl propyl carbonate (3.2 g) and acetonitrile (1 ml) was stirred for 12 hours at 100° C. After having been cooled, the mixture was diluted with diisopropyl ether (10 ml), and the resulting powder was collected by filtration. The powder was subjected to silica gel chromatography (eluent: ethyl acetate→acetone→acetone/ethanol=10/→acetone/ethanol=5/1). The solvent was distilled off, and the residue was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium chloride (Compound 19, 0.02 g) as a white powder.

$^1$H-NMR (d$_6$-DMSO) δ: 0.88 (3H, t, J=7.8 Hz), 0.97 (3H, d, J=7.0 Hz), 1.62 (2H; tq, J=7.8 Hz), 3.63–3.67 (1H, m), 3.80–4.05 (3H, m), 4.09 (2H, t, J=7.8 Hz), 4.69 (1H, q, J=7.0 Hz), 4.88 (1H, d, J=14.4 Hz), 5.05 (1H, d, J=14.4 Hz), 6.13 (1H, d, J=10.6 Hz), 6.21 (1H, d, J=10.6 Hz), 6.52 (1H, s), 6.94–7.02 (1H, m), 7.24–7.33 (2H, m), 7.90 (4H, s), 9.10 (1H, s), 10.05 (1H, s), 10.39 (1H, s).

Reference Example 29

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1 g), iodomethyl propyl carbonate (0.9 g) and acetonitrile (15 ml) was stirred for 12 hours at 50–55° C. The mixture was subjected to silica gel chromatography (eluent: ethyl acetate/hexane=5/1→ethyl acetate→acetone→acetone/ethanol=10/1→acetone/ethanol=5/1) and then ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium iodide (Compound 20, 1 g) as a pale yellow powder.

$^1$H-NMR (d$_6$-DMSO) δ: 0.88 (3H, t, J=7.2 Hz), 0.98 (3H, d, J=7.2 Hz), 1.61 (2H, tq,J=7.2 Hz), 3.50–3.70 (1H, m), 3.84–4.13 (3H, m), 4.09 (2H, t, J=7.2 Hz), 4.68 (1H, q, J=7.2 Hz), 4.86 (1H, d, J=13.8 Hz), 4.96 (1H, d, J=13.8 Hz), 6.12 (1H, d, J=11H,z), 6.20 (1H, d, J=11H,z), 6.33 (1H, s), 6.97–7.07 (1H, m), 7.21–7.38 (2H, m), 7.90 (4H, s), 9.11 (1H, s), 10.05 (1H, s), 10.21 (1H, s).,

Reference Example 30

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium iodide (Compound 20, 0.3 g) was dissolved in a mixture of tetrahydrofuran and ethyl acetate (3/1) (100 ml), and the solution was washed four times with saturated aqueous solution (50 ml) of sodium chloride. The organic layer was dried over magnesium sulfate, and the solvent was distilled off. The residue was crystallized from ethanol/acetone to give 1-[(2R,3R)-2-(2,4-difluorophenyl)-2-hydroxy-3-[2-oxo-3-[4-(1H-tetrazol-1-yl)phenyl]-1-imidazolidinyl] butyl]-4-propoxycarbonyloxymethyl-1H-1,2,4-triazolium chloride (Compound 19, 0.09 g) as a white powder.

Elemental Analysis: $C_{27}H_{30}ClF_2N_9O_5 \cdot 0.5H_2O$

Calcd.(%): C; 50.43, H; 4.86, N; 19.60, Cl; 5.51,

Found (%): C; 50.25, H; 4.71, N; 19.31, Cl; 5.42.

Reference Example 31

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.80 g) and chloromethyl propanate (4.07 g) was added acetonitrile (1.6 ml), and the mixture was stirred for 12 hours at 100° C. under an argon atmosphere. The reaction mixture was concentrated under reduced pressure, and to the residue was added diisopropyl ether (8 ml). The resulting powder was collected by filtration. The powder was subjected to silica gel flush chromatography (eluent: ethyl acetate→acetone→acetone/ethanol=9/1→4/1), and a fraction containing the desired compound was concentrated under reduced pressure. The residue was subjected to ODS column chromatography (eluent: methanol/water=3/2). The eluate was concentrated in vacuo, and the residue was dissolved in water (10 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-propanoyloxymethyl-1H-1,2,4-triazolium chloride (Compound 13, 0.11 g) as a white powder.

$^1$H-NMR($d_6$-DSMO) δ: 0.92–1.12(6H,m), 2.25–2.55(2H, m), 3.60–4.10(4H,m), 4.64–4.75(1H,m), 4.86(1H,d,J=14 Hz), 5.08(1H,d,J=14 Hz), 6.09–6.21(2H,m), 6.64(1H,s), 6.96–7.06(1H,m), 7.22–7.42(2H,m), 7.80–8.02(5H,m), 8.80 (1H,brs), 9.07(1H,s), 10.42(1H,s).

Reference Example 32

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.80 g) and chloromethyl propanate (4.07 g) was added acetonitrile (1.6 ml), and the mixture was stirred for 10 hours at 100° C. under an argon atmosphere. The reaction mixture was concentrated under reduced pressure, and to the residue was added diisopropyl ether (8 ml). The resulting powder was collected by filtration. The powder was subjected to silica gel flush chromatography (eluent: ethyl acetate→acetone→acetone/ethanol=9/1→5/1), and the fraction containing the desired compound was concentrated under reduced pressure. The residue was subjected to ODS column chromatography (eluent: methanol/water=3/2). The eluate was concentrated in vacuo, and the residue was dissolved in water (10 ml). The solution was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propanoyloxymethyl-1H-1,2,4-triazolium chloride (Compound 14, 0.04 g) as a white powder.

$^1$H-NMR($d_6$-DSMO) δ: 0.97(3H,d,J=7 Hz), 1.01(3H,t,J=7.4 Hz), 2.38(2H,q,J=7.4 Hz), 3.61–4.09(4H,m), 4.65–4.75 (1H,m), 4.86(1H,d,J=14 Hz), 5.08(1H,d,J=14 Hz), 6.11(1H, d,J=11H,z), 6.19(1H,d,J=11H,z), 6.61(1H,s), 6.96–7.06(1H, m), 7.25–7.49(2H,m), 7.90(4H,s), 9.07(1H,s), 10.07(1H,s), 10.40(1H,s).

Reference Example 33

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.50 g) and chloromethyl ethyl carbonate (2.9 g) was added acetonitrile (0.5 ml), and the mixture was stirred for 22 hours at 100° C. The reaction mixture was concentrated under reduced pressure. To the residue was added diisopropyl ether (10 ml), and the resulting powder was collected by filtration. The powder was subjected to silica gel flush chromatography (eluent: ethyl acetate/acetone=1/1→acetone→acetone/ethanol=9/1→4/1), and the fraction containing the desired compound was concentrated under reduced pressure. The residue was subjected to ODS column chromatography (eluent: methanol/water=3/2). The eluate was concentrated in vacuo, and the residue was dissolved in water(15 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-ethoxycarbonyloxymethyl-1H-1,2,4-triazolium chloride (Compound 15, 0.14 g) as a white powder.

$^1$H-NMR($d_6$-DSMO) δ: 0.97(3H,d,J=7 Hz), 1.22(3H,t, J=7 Hz), 3.60–4.08(4H,m), 4.18(2H,q,J=7 Hz), 4.63–4.73 (1H,m), 4.87(1H,d,J=14 Hz), 5.10(1H,d,J=14 Hz), 6.13(1H, d,J=11H,z), 6.21(1H,d,J=11H,z), 6.65(1H,s), 6.96–7.04(1H, m), 7.24–7.37(2H,m), 7.82–7.95(5H,m), 8.78(1H,d,J=1H, z), 9.09(1H,s), 10.48(1H,s).

Reference Example 34

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(1.31 g) and ethyl iodomethyl carbonate (1.25 g) was added acetonitrile (20 ml) and the mixture was stirred for 14 hours at 60° C. under an argon atmosphere. The reaction mixture was concentrated under reduced pressure and the residue was submitted to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-ethoxycarbonyloxymethyl-1H-1,2,4-triazolium iodide (Compound 17, 1.1 g) as a pale yellow powder.

$^1$H-NMR($d_6$-DSMO) δ: 0.99(3H,d,J=7 Hz), 1.23(3H,t, J=7 Hz), 3.64–4.05(4H,m), 4.19(2H,q,J=7 Hz), 4.64–4.74 (1H,m), 4.87(1H,d,J=14 Hz), 4.97(1H,d,J=14 Hz), 6.13(1H, d,J=11H,z), 6.21(1H,d,J=11H,z), 6.33(1H,br), 6.99–7.07 (1H,m), 7.22–7.39(2H,m), 7.91(4H,s), 9.12(1H,s), 10.06 (1H,s), 10.23(1H,s).

Reference Example 35

1-[(2R,3R)-2-(2,4-Difluorophenyl)-2-hydroxy-3-[2-oxo-3-[4-(1H-tetrazol-1-yl)phenyl]-1-imidazolidinyl]butyl]-4- ethoxycarbonyloxymethyl-1H-1,2,4-triazolium iodide (Compound 17, 1.10 g) was subjected to ion-exchange chromatography (DOWEX 1×8, Cl⁻ type, 300 ml), and the fraction containing the desired compound was concentrated under reduced pressure. The residue was recrystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-ethoxycarbonyloxymethyl-1H-1,2,4-triazolium chloride (Compound 16, 0.70 g) as colorless powdery crystals.

¹H-NMR($d_6$-DSMO) δ: 0.97(3H,d,J=7 Hz), 1.22(3H,t, J=7 Hz), 3.60–4.08(4H,m), 4.18(2H,q,J=7 Hz), 4.63–4.73 (1H,m), 4.87(1H,d,J=14 Hz), 5.10(1H,d,J=14 Hz), 6.13(1H, d,J=11H,z), 6.21(1H,d,J=11H,z), 6.66(1H,s), 6.96–7.04(1H, m), 7.24–7.36(2H,m), 7.90(4H,s), 9.09(1H,s), 10.07(1H,s), 10.48(1H,s).

Reference Example 36

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g), chloromethyl isopropyl carbonate (3.17 g) and acetonitrile (1 ml) was stirred for 6 hours at 100° C. After having been cooled, the mixture was diluted with diisopropyl ether (10 ml). The resulting powder was collected by filtration. The powder was subjected to silica gel chromatography (eluent: ethyl acetate→acetone→acetone/ethanol=10/1→acetone/ethanol=5/1). The solvent was distilled off, and the residue was crystallized from ethanol/acetone to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-(isopropoxycarbonyloxy)methyl-1H-1,2,4-triazolium chloride (Compound 18, 110 mg) as white powdery crystals.

¹H-NMR ($d_6$-DMSO) δ: 0.98 (3H, d, J=7.4 Hz), 1.24 (6H, d, J=6.2 Hz), 3.62–3.66 (1H, m), 3.98–4.0 (3H, m), 4.69 (1H, q, J=7.4 Hz), 4.80 (1H, quintet, J=6.2 Hz), 4.87 (1H, d, J=14.4 Hz), 5.04 (1H, d, J=14.4 Hz), 6.11 (1H, d, J=11H,z), 6.19 (1H, d, J=11H,z), 6.51 (1H, s), 6.96–7.03 (1H, m), 7.22–7.38 (2H, m), 7.90 (4 H, s), 9.10 (1H, s), 10.06 (1H, s), 10.36 (1H,s).

Reference Example 37

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (2.5 g) and (1,3-dioxan-5-yl)iodomethyl carbonate (3 g) was added acetonitrile (40 ml), and the mixture was stirred for 12 hours at 50–55° C. The mixture was subjected to silica gel chromatography (eluent: ethyl acetate/hexane=1/1→ethyl acetate/hexane=10/1→ethyl acetate→acetone→acetone/ethanol=5/1) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(1,3-dioxan-5-yl)oxycarbonyloxymethyl]-1H-1,2,4-triazolium iodide (Compound 31, 4.22 g) as a yellow powder.

¹H-NMR ($d_6$-DMSO) δ: 0.98 (3H, d, J=7 Hz), 3.55–3.75 (1H, m), 3.87–4.02 (7H, m), 4.50–4.58 (1H, m), 4.67–4.93 (5H, m), 6.16 (1H, d, J=11H,z), 6.24 (1H, d, J=11H,z), 6.33 (1H, s), 6.97–7.07 (1H, m), 7.21–7.39 (2H, m), 7.90 (4H, s), 9.12 (1H, s), 10.05 (1H, s), 10.23 (1H, s).

Reference Example 38

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[(1–3-dioxan-5-yl)oxycarbonyloxymethyl]-1H-1,2,4-triazolium iodide (Compound 31, 1 g) was subjected to ion-exchange resin [Dowex 1×8 (Cl⁻ type)] (eluent: water), and the eluate was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(1,3-dioxan-5-yl)oxycarbonyloxymethyl]-1H-1,2,4-triazolium chloride (Compound 22, 0.23 g) as a white powder.

¹H-NMR ($d_6$-DMSO) δ: 0.97 (3H, d, J=6.6 Hz), 3.63–3.66 (1H, m), 3.87–4.02 (7H, m), 4.52–4.59 (1H, m), 4.60–5.11 (5H, m), 6.17 (1H, d, J=11H,z), 6.25 (1H, d, J=11H,z), 6.59 (1H, s), 6.97–7.04 (1H, m), 7.23–7.40 (2H, m), 7.90(4H,s),9.11 (1H, s), 10.06 (1H, s), 10.44 (1H, s).

The lyophilized product (0.15 g) of Compound 22 obtained above was crystallized from ethanol(20 ml) to give white crystals of Compound 22 (0.14 g).

Elemental Analysis: $C_{28}H_{30}ClF_2N_9O_7$
Calcd.(%): C, 49.60; H, 4.46; N, 18.59
Found (%): C, 49.60; H, 4.46; N, 18.40

Reference Example 39

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(0.50 g) and chloromethyl [(1S)-1-(ethoxycarbonyl)ethyl] carbonate (1.09 g) was added acetonitrile (5 ml), and the mixture was stirred for 68 hours at 95° C. The reaction mixture was concentrated under reduced pressure. To the residue was added diisopropyl ether (6 ml), and the resulting powder was collected by filtration. The powder was subjected to silica gel flush chromatography (eluent: ethyl acetate→ethyl acetate/acetone=1/1→acetone→acetone/ethanol=5/1). The fraction containing the desired compound was concentrated under reduced pressure. The residue was subjected to ODS column chromatography (eluent: methanol/water=3/2). The eluate was concentrated in vacuo and dissolved in water (50 ml). The solution was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(1S)-1-ethoxycarbonylethoxy]carbonyloxymethyl]-1H-1,2,4-triazolium chloride (Compound 23,0.22 g) as a white powder.

¹H-NMR($d_6$-DMSO) δ: 0.98(3H,d,J=7 Hz), 1.17(3H,t, J=7 Hz), 1.43(3H,d,J=7 Hz), 3.60–4.08(4H,m), 4.14(2H,q, J=7 Hz.), 4.65–4.75(1H,m), 4.86(1H,d,J=14 Hz), 5.02(1H, q,J=7 Hz), 5.11(1H,d,J=14 Hz), 6.24(2H,s), 6.65(1H,s), 6.95–7.05(1H,m), 7.25–7.39(2H,m), 7.90(4H,s), 9.11(1H,s), 10.07(1H,s), 10.52(1H,s)

Reference Example 40

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) and [(1S)-1-(benzyloxycarbonyl)ethyl]iodomethyl carbonate (1.53 g) was added acetonitrile (15 ml), and the mixture was stirred for 12 hours at 60° C. under an argon atmosphere. The reaction mixture was concentrated under reduced pressure and the residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and subjected to ion-exchange chromatography (DOWEX 1×8, Cl⁻ type). The fraction containing the desired compound was concentrated under reduced pressure to give 1-[(2R,3R)-2-(2,4-difluorophenyl)-2- hydroxy-3-[2-oxo-3-[4-(1H-tetrazol-1-yl)phenyl]-1-imidazolidinyl]butyl]-4-[[(1S)-1-(benzyloxycarbonylethoxy]carbonyloxymethyl]-1H-1,2,4-triazolium chloride (Compound 24, 0.25 g) as a white powder.

$^1$H-NMR($d_6$-DMSO) δ: 0.97(3H,d,J=7.0 Hz), 1.45(3H,d, J=6.6 Hz), 3.60–4.08(4H,m), 4.65–4.78(1H,m), 4.85(1H,d, J=14 Hz), 5.07–5.18(4H,m), 6.23(2H,s), 6.67(1H,s), 6.95–7.04(1H,m), 7.24–7.37(7H,m), 7.9(4H,s), 9.09(1H,s), 10.07(1H,s), 10.53(1H,s)

Reference Example 41

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(2.0 g) and (3-benzyloxypropyl) iodomethyl carbonate(2.9 g) was added acetonitrile (20 ml), and the mixture was stirred for 20 hours at 50 to 55° C. under an argon atmosphere. The reaction mixture was concentrated under reduced pressure. The residue was dissolved in a mixture of ethyl acetate (100 ml) and tetrahydrofuran (50 ml). To the solution was added a mixture of saturated aqueous solution of sodium chloride (50 ml) and 5% aqueous solution of sodium thiosulfate (0.1 ml), and the mixture was shaken. The organic layer was washed with saturated aqueous solution of sodium chloride (50 ml) four times. The organic layer was dried over anhydrous magnesium sulfate, and the solvent was distilled off. The residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and then the eluate was subjected to ion-exchange chromatography (DOWEX 1×8, Cl⁻ type). The fraction containing the desired compound was concentrated under reduced pressure to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-benzyloxypropoxy)carbonyloxymethyl]-1H-1,2,4-triazolium chloride (Compound 25, 0.79 g) as a white powder.

$^1$H-NMR($d_6$-DMSO) δ: 0.97(3H,d,J=7.2 Hz), 1.89(2H, quintet,J=6.4 Hz), 3.47(2H,t, J=6.2 Hz), 3.60–4.09(4H,m), 4.22(2H,t,J=6.6 Hz), 4.44(2H,s), 4.65–4.75(1H,m), 4.86 (1H,d,J=14 Hz), 5.09(1H,d,14 Hz), 6.12(1H,d,J=11H,z), 6.20(1H,d,J=11H, z), 6.62(1H,s), 6.94–7.04(1H,m), 7.24–7.36(7H,m), 7.9(4H,s), 9.09(1H,s), 10.07 (1H,s), 10.45 (1H,s)

Reference Example 42

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[(3-benzyloxypropoxy)carbonyloxymethyl]-1H-1,2,4-triazolium chloride(Compound 25, 0.66 g) was dissolved in methanol (25 ml), and to the solution were added 1N-hydrochloric acid (0.89 ml) and 10% palladium-carbon (50% wet, 0.33 g). The mixture was stirred for 1.5 hours at room temperature under a hydrogen atmosphere. The catalyst was filtered off, and the filtrate was concentrated under reduced pressure. The residue was subjected to ODS column chromatography (eluent: methanol/water=3/2) and recrystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-hydroxypropoxy)carbonyloxymethyl]-1H-1,2,4-triazolium chloride (Compound 26, 0.19 g) as colorless powdery crystals.

$^1$H-NMR($d_6$-DSMO) δ: 0.98(3H,d,J=7 Hz), 1.74(2H, quintet,J=6 Hz), 3.44(2H,dt, J=6 Hz,5 Hz), 3.60–4.10(4H, m), 4.20(2H,t,J=6 Hz), 4.59(1H,t,J=5 Hz), 4.65–4.75 (1H, m), 4.87(1H,d,J=14 Hz), 5.10(1H,d,J=14 Hz), 6.13(1H,d,J= 11H,z), 6.21(1H, d,J=11H,z), 6.63(1H,s), 6.95–7.05(1H,m), 7.25–7.37(2H,m), 7.89(4H,s), 9.09 (1H,s), 10.06(1H,s), 10.48(1H,s).

Reference Example 43

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.6 g) and iodomethyl [(4S)-2,2-dimethyl-1,3-dioxolan-4-yl]methyl carbonate (2.1 g) was added to acetonitrile (20 ml), and the mixture was stirred for 15 hours at 55° C. The resulting mixture was subjected to silica gel chromatography (eluent: ethyl acetate→acetone→acetone/ethanol=5/1), and then the eluate was subjected to ion-exchange resin (Dowex 1×8, Cl⁻) (eluent: water). The eluate was evaporated in vacuo, and the residue was subjected to ODS column chromatography (eluent: methanol/water=3/2). The solvent was distilled off under reduced pressure, and the residue was crystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(4S)-2,2-dimethyl-1,3-dioxolan-4-yl]methyloxycarbonyloxymethyl]-1H-1,2,4-triazolium chloride (Compound 27, 0.4 g) as white crystals.

$^1$H-NMR($d_6$-DMSO) δ: 0.98(3H,d,J=7.0 Hz), 1.26(3H,s), 1.30(3H,s), 3.62–3.72(2H,m), 3.97–4.34(7H,m), 4.70(1H,q, J=7.0 Hz), 4.88(1H,d,J=14.2 Hz), 5.12(1H,d,14.2 Hz), 6.16 (1H,d,J=11.0 Hz), 6.24(1H,d,J=11.0 Hz), 6.66(1H,s), 6.94–7.03(1H,m), 7.21–7.38(2H,m), 7.89(4H,s), 9.10(1H,s), 10.05(1H,s), 10.51(1H,s)

Reference Example 44

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[[(4S)-2,2-dimethyl-1,3-dioxolan-4-yl]methyloxycarbonyloxymethyl]-1H-1,2,4-triazolium chloride (Compound 27, 0.1 g) was dissolved in tetrahydrofuran (1.5 ml), and to the solution was added 1-N hydrochloric acid solution (1.5 ml) under ice cooling. The mixture was stirred for 4 hours at room temperature. The resulting mixture was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(2S)-2,3-dihydroxypropoxy]carbonyloxymethyl]-1H-1,2,4-triazolium chloride (Compound 28, 0.05 g) as a white powder.

$^1$H-NMR ($d_6$-DMSO) δ: 0.98 (3H,d,J=7.0 Hz), 3.26–4.24 (9H,m), 4.70 (1H,q, J=7.0 Hz), 4.86 (1H,d,J=14.6 Hz), 5.09 (1H,d,J=14.6 Hz), 6.15 (1H,d,J=11.0 Hz), 6.22 (1H,d,J=11.0 Hz), 6.63 (1H,s), 6.96–7.06 (1H,m), 7.23–7.36 (2H,m), 7.90 (4H,s), 9.10 (1H,s), 10.06 (1H,s), 10.46 (1H,s).

Reference Example 45

To a solution of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) in acetonitrile (15 ml) was added (3-benzyloxycarbonylpropyl) iodomethyl carbonate (1.0 g) under a nitrogen atmosphere, and the mixture was stirred for 20 hours at 45–50 C. The reaction mixture was concentrated under reduced pressure. The residue was subjected to silica gel column chromatography (eluent: ethyl acetate→acetone ), and a fraction containing the desired compound was concentrated under reduced pressure. The residue was subjected to ODS column chromatography (eluent: methanol/water=3/2) to give 4-[(3-benzyloxycarbonylpropoxy)carbonyloxymethyl]-1-[(2R, 3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium iodide (Compound 32, 1.47 g) as a yellow powder.

$^1$H-NMR (d$_6$-DMSO) δ: 1.04 (3H,d,J=7 Hz), 1.83–1.97 (2H,m), 2.45 (2H,t, J=7 Hz), 3.57–3.69 (2H,m), 3.90–4.09 (2H,m), 4.18 (2H,t, J=7 Hz), 4.69 (1H,q, J=7 Hz), 4.87 (1H,d,J=14 Hz), 4.98 (1H,d,J=14 Hz), 5.08 (2H,s), 6.14 (1H,d,J=11 H,z), 6.22 (1H,d,J=11H,z), 6.33 (1H,s), 6.99–7.08 (1H,m), 7.23–7.32 (2H,m), 7.35 (5H,s), 7.91 (4H,s), 9.12 (1H,s), 10.07 (1H,s), 10.24 (1H,s).

Reference Example 46

4-[(3-Benzyloxycarbonylpropoxy)carbonyloxymethyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium iodide (Compound 32, 1.47 g) was subjected to ion-exchange chromatography (Dowex 1×8, Cl$^-$ type, 500 ml), and a fraction containing the desired product was concentrated under reduced pressure to give 4-[(3-benzyloxycarbonylpropoxy)carbonyloxy-methyl]-1-[(2R, 3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 29, 893 mg) as a white powder.

$^1$H-NMR (d$_6$-DMSO) d:1.04 (3H,d,J=7 Hz), 1.82–1.99 (2H,m), 2.44 (2H,t, J=7 Hz), 3.53–3.67 (2H,m), 3.95–4.03 (2H,m), 4.17 (2H,t, J=7 Hz), 4.68 (1H,q, J=7 Hz), 4.87 (1H,d,J=14 Hz), 5.06 (1H,d,J=14 Hz), 5.07 (2H,s), 6.13 (1H,d,J=11H,z), 6.21 (1H,d,J=11H,z), 6.56 (1H,s), 6.95–7.05 (1H,m), 7.23–7.33 (2H,m), 7.34 (5H,s), 7.90 (4H,s), 9.09 (1H,s), 10.07 (1H,s), 10.41 (1H,s).

Reference Example 47

4-[(3-Benzyloxycarbonylpropoxy)carbonyloxymethyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 29, 155 mg) was dissolved in methanol (6 ml). To the solution were added 1N hydrochloric acid solution (0.2 ml) and 10% palladium-carbon (50% wet, 77 mg). The mixture was stirred for 0.5 hours at room temperature under a hydrogen atmosphere. The catalyst was filtered off, and to the filtrate was added distilled water. The mixture was concentrated under reduced pressure, and the concentrate was lyophilized to give 1-[(2R, 3R)-2-(2,4-difluorophenyl)-2-hydroxy-3-[2-oxo-3-[4-(1H-tetrazol-1-yl)phenyl]-1-imidazolidinyl]butyl]-4-[(3-carboxypropoxy)carbonyloxymethyl]-1H-1,2,4-triazolium chloride (Compound 33, 122 mg) as a white powder.

$^1$H-NMR (d$_6$-DMSO) d:0.98 (3H,d,J=7 Hz), 1.78–1.90 (2H,m), 2.29 (2H,t, J=7 Hz), 3.54–3.69 (2H,m), 3.94–4.04 (2H,m), 4.16 (2H,t, J=7 Hz), 4.69 (1H,q, J=7 Hz), 4.87 (1H,d,J=14 Hz), 5.06 (1H,d,J=14 Hz), 6.13 (1H,d,J=11H,z), 6.21 (1H,d,J=11H,z), 6.54 (1H,s), 6.95–7.10 (1H,m), 7.24–7.37 (2H,m), 7.90 (4H,s), 8.31 (1H,s), 9.09 (1H,s), 10.06 (1H,s), 10.34 (1H,s).

Reference Example 48

A solution of bromomethyl acetate (2.4 g) and sodium iodide (2.3 g) in acetonitrile (75 ml) was stirred for 2 hours at 80° C. The reaction mixture was cooled to room temperature, and the resulting crystals were filtered off, and to the filtrate was added 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (5 g). The mixture was stirred for 16 hours at 45° C. The precipitates in the reaction mixture were filtered off, and the solvent was distilled off. The residue was dissolved in tetrahydrofuran (150 ml). The solution was washed with a mixture of saturated aqueous solution of sodium chloride (150 ml) and 5% aqueous solution of sodium thiosulfate (10 ml). The organic layer was washed twice with saturated aqueous solution of sodium chloride (150 ml). The tetrahydrofuran layer was dried over anhydrous magnesium sulfate, and the solvent was distilled off. To the residue was added ethanol (50 ml), and solvent was distilled off. To the residue were added acetone (3 ml) and ethanol (1.3 ml), and the mixture was allowed to stand for 2 hours at 0° C. To the resulting white solid was added ethanol (3 ml). The solid was collected by filtration and dried under reduced pressure. The resulting white powder was dissolved in a mixture of tetrahydrofuran (400 ml) and methanol (70 ml). The solution was washed with a saturated aqueous solution of sodium chloride (250 ml) seven times. The organic layer was dried over anhydrous magnesium sulfate and the solvent was distilled off under reduced pressure. The residue was dissolved in a mixture of ethanol (150 ml) and acetone (50 ml), and the solvent was distilled of under reduced pressure. To the residue was added ethanol (100 ml) and the solvent was again distilled off under reduced pressure. To the residue was added a mixture of ethanol (150 ml) and acetone (50 ml). The solvent was distilled off to make the volume of the solution of 20 ml, and the solution was allowed to stand for 2 hours at room temperature. The resulting solid was collected by filtration to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 3.6 g) as white crystals. The physicochemical properties of this product were identical with those of the crystals of Compound 12 obtained by crystallization from ethanol in Reference Example 24.

Reference Example 49

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (2.0 g) and [2-(acetylamino)ethyl] iodomethyl carbonate (2.9 g) was added acetonitrile (20 ml), and the mixture was stirred for 20 hours at 50 to 55° C. under an argon atmosphere. The reaction mixture was concentrated under reduced pressure. The residue was dissolved in a mixture of ethyl acetate (100 ml) and tetrahydrofuran (50 ml). To the mixture was added a mixture of saturated aqueous solution of sodium chloride (50 ml) and 5% aqueous solution of sodium thiosulfate (0.1 ml), and the mixture was shaken. The organic layer was washed 4 times with saturated aqueous solution of sodium chloride (50 ml). The organic layer was dried over anhydrous magnesium sulfate, and the solvent was distilled off. The residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and the eluate was subjected to ion-exchange chromatography (Dowex 1×8, Cl$^-$type). The fraction containing the desired compound was concentrated under reduced pressure to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2-acetylaminoethoxy)carbonyloxymethyl]-1H-1,2,4-triazolium chloride (Compound 34, 0.50 g) as a white powder.

¹H-NMR(d₆-DMSO) δ: 0.97(3H,d,J=7 Hz),1.77(3H,s), 3.30(2H,q,J=6 Hz),3.60–3.72(1H,m),3.92–4.08(3H,m),4.12 (2H,t,J=6 Hz),4.65–4.75(1H,m), 4.87(1H,d, J=14 Hz), 5.10 (1H,d,J=14 Hz), 6.14(1H,d,J=11H,z),6.23(1H,d,J=11H,z), 6.63 (1H, s), 6.95–7.05(1H,m), 7.26–7.37(2H,m), 7.90(4H, s), 8.09(1H,t,J=6 Hz), 9.10 (1H,s), 10.07 (1H,s), 10.49(1H, s).

Reference Example 50

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) and iodomethyl [3-(methoxy)propyl] carbonate(1.1 g) was added acetonitrile (10 ml), and the mixture was stirred for 15 hours at 40 to 50° C. under an argon atmosphere. The reaction mixture was concentrated under reduced pressure. The residue was dissolved in a mixture of acetonitrile (5 ml) and ethyl acetate (100 ml). The solution was shaken with a mixture of saturated aqueous solution of sodium chloride (50 ml) and 5% aqueous solution of sodium thiosulfate (0.1 ml). The organic layer was washed four times with saturated aqueous solution of sodium hydrogen chloride (50 ml). The organic layer was dried over anhydrous magnesium sulfate, and the solvent was distilled off under reduced pressure. The residue was subjected to silica gel flush chromatography (eluent: ethyl acetate→acetone→acetone/ethanol=4/1). The fraction containing the desired compound was concentrated under reduced pressure.

The residue was subjected to ion-exchange chromatography (Dowex 1×8, Cl⁻type), and then the eluate was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-methoxypropoxy) carbonyloxymethyl]-1H-1,2,4-triazolium chloride (Compound 35, 0.80 g) as a white powder.

¹H-NMR(d₆-DMSO) δ: 0.97(3H,d,J=7 Hz), 1.83(2H, quintet,J=6 Hz), 3.20(3H,s) 3.35(2H,t,J=6 Hz), 3.55–3.70 (1H,m), 3.90–4.10(3H,m), 4.18(2H,t,J=6 Hz), 4.64–4.75 (1H,m), 4.87(1H,d,J=14 Hz), 5.11(1H,d,J=14 Hz), 6.14(1H, d,J=11H,z), 6.22(1H,d,J=11H,z), 6.66(1H,s), 6.95–7.05(1H, m), 7.25–7.39(2H,m), 7.90(4H,s), 9.10(1H,s), 10.07(1H,s), 10.48(1H,s).

Reference Example 51

A solution of bromomethyl acetate (424 mg) and sodium iodide (415 mg) in acetonitrile (15 ml) was stirred for 2 hours at 80° C. The reaction mixture was cooled to room temperature, and residual sodium bromide was filtered off. To the filtrate was added 2-[(1R,2R)-2-(2,4-difluorophenyl)-2-hydroxy-1-methyl-3-(1H-1,2,4-triazol-1-yl)propyl]-4-[4-(2,2,3,3-tetrafluoro-propoxy)phenyl]-3(2H,4H)-1,2,4-triazolone (1 g), and the mixture was stirred for 16 hours at 45° C. The precipitate in the reaction mixture was filtered off, and the solvent was distilled off under reduced pressure. The residue was dissolved in tetrahydrofuran (30 ml), and washed with a mixture of saturated aqueous solution of sodium chloride (30 ml) and 5% aqueous solution of sodium thiosulfate (2 ml), and then washed twice with saturated aqueous solution of sodium chloride (30 ml). The tetrahydrofuran layer was dried over anhydrous magnesium sulfate, and the solvent was distilled off under reduced pressure. The residue was subjected to silica gel chromatography (eluent: ethyl acetate→ethyl acetate/ethanol=10/1→4/1) and then subjected to ion-exchange resin [Dowex 1×8 (Cl⁻type)] (eluent: water). A fraction containing the desired product was lyophilized to give 4-acetoxymethyl-1-[(2R,3R)-2-(2, 4-difluorophenyl)-2-hydroxy-3-[4,5-dihydro-5-oxo-4-[4-(2, 2,3,3-tetrafluoropropoxy)phenyl]-1H-1,2,4-triazol-1-yl] butyl-1H-1,2,4-triazolium chloride (Compound 36, 294 mg) as a white powder.

¹H-NMR(d₆-DMSO) δ: 1.22 (3H, d, J=7 Hz), 2.08 (3H, s), 4.66 (2H, t, J=14 Hz), 4.85 (1H, d, J=14 Hz), 4.89 (1H, q, J=7 Hz), 4.98 (1H, d, J=14 Hz), 6.09 (1H, d, J=11H,z), 6.19 (1H, d, J=11H,z), 6.26 (1H, s), 6.69 (1H, tt, J=52, 5 Hz), 6.97–7.06 (1H, m), 7.23 (2H, d, J=9 Hz), 7.25–7.41 (2H, m), 7.69 (2H, d, J=9 Hz), 8.58 (1H, s), 9.09 (1H, s), 10.25 (1H, s).

Reference Example 52

A solution of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (200 mg) and bromomethyl acetate (77.1 mg) in acetonitrile (2 ml) was stirred for 7 hours at 80° C. under an argon atmosphere. The reaction mixture was diluted with acetonitrile (11 ml), and the resulting mixture was stirred at 80° C. until the crystals precipitated in the mixture were dissolved. After having been cooled to room temperature, silica gel (400 mg) was added, and the mixture was stirred for 10 minutes at room temperature. The silica gel was filtered off and washed with a mixture of acetonitrile and tetrahydrofuran (1/1, 2 ml×3). The mother liquor and the washings were combined, and a saturated aqueous solution of sodium chloride (10 ml) was added. The resulting mixture was stirred for 30 minutes at room temperature, and the organic layer was separated. The same operation, the addition of a saturated aqueous solution of sodium chloride (10 ml) followed by the stirring for 30 minutes at room temperature and the subsequent separation of the organic layer, was further performed three times. The organic layer was dried over anhydrous magnesium sulfate, and the solvent was distilled off under reduced pressure. The residue was dissolved in tetrahydrofuran (3 ml), and the solution was allowed to stand for 5 hours at room temperature. The precipitated solid (179 mg) was collected by filtration and dissolved in a mixture of methanol and tetrahydrofuran (1/1, 4 ml). The solution was concentrated under reduced pressure and the residue was dissolved in tetrahydrofuran (2 ml). The solution was allowed to stand for 5 hours at room temperature. The precipitated powdery crystals (167 mg) was collected by filtration and dissolved in a mixture of ethanol (6 ml) and acetone (0.5 ml). The solution was concentrated under reduced pressure to a volume of ca. 2 ml and allowed to stand for 3 hours at room temperature. The solid precipitated was collected by filtration to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 126 mg) as white crystals. The physicochemical properties of this product were identical with those of the crystals of Compound 12 obtained by crystallization from ethanol in Reference Example 24.

Comparative Example

The stability of a lyophilized pharmaceutical preparation prepared from compound 12 obtained in Reference Example 24 without adding the additive of the present invention is shown in this example. A solution was prepared according to the prescription (per vial) in Table 2 and introduced into a 9 p vial. The lyophilization conditions are shown below. The sample was frozen at −50 ° C. or less for about 2 hours, and after the temperature was increased to −10° C. at a rate of 10° C./hr, the sample was subjected to primary lyophilization for 12 hours. Thereafter, the temperature was increased to 45° C. at a rate of 10° C./hr, and the sample was subjected to secondary lyophilization for 6 hours. The degree of vacuum was 0.05 Torr throughout the entire process. For returning to the atmospheric pressure, low-moisture nitrogen was used. The water content of each product as determined by the Karl Fisher method was 0.78% for prescription 1 and 0.95% for prescription 2. The results in the stability test are as shown in Table 3, indicating that these products was very labile.

TABLE 2

Prescriptions for Lyophilization in the Comparative Example

|  | Prescription 1 | Prescription 2 |
| --- | --- | --- |
| Compound 12 | 12.25 mg | 12.25 mg |
| Injection water | 2 ml | — |
| 10 mM citric acid buffer (pH 4) | — | 2 ml |

TABLE 3

Results of the Stability Test (Residual Compound 12 (%))

|  | Prescription 1 | Prescription 2 |
| --- | --- | --- |
| 60° C., 2 weeks | 66.0 | 75.7 |
| 60° C., 1 month | 49.5 | 48.9 |
| 40° C., 1 month | 90.6 | 91.3 |
| 40° C., 2 months | 79.7 | 85.6 |
| 40° C., 4 months | 63.3 | 80.1 |

Example 1

Lyophilized pharmaceutical preparations were prepared by mixing Compound 12 obtained in Reference Example 24 with an additive (lactose, white sugar or maltose) in a ratio shown in Table 4. The lyophilization conditions were the same as in the Comparative Example. The water content of each product as determined by the Karl Fisher method was 0.89% for prescription 3, 0.3% for prescription 4 and 0.3% for prescription 5. In the stability test, the results in Table 5 were obtained. The stability of the pharmaceutical compositions of the present invention was improved significantly as compared with that of the Comparative Example.

TABLE 4

Stabilized Prescriptions for Lyophilization

|  | Prescription 3 | Prescription 4 | Prescription 5 |
| --- | --- | --- | --- |
| Compound 12 | 12.25 mg | 12.25 mg | 12.25 mg |
| Lactose | 100 mg | — | — |
| White sugar | — | 5 mg | — |
| Maltose | — | — | 3 mg |
| Injection water | 2 ml | 2 ml | 2 ml |

TABLE 5

Results of the Stability Test (Residual Compound 12 (%))

|  | Prescription 3 | Prescription 4 | Prescription 5 |
| --- | --- | --- | --- |
| 60° C., 2 weeks | 95.5 | 101.1 | 103.3 |
| 60° C., 1 month | 96.3 | — | 98.1 |
| 40° C., 1 month | 96.3 | 104.1 | 102.4 |
| 40° C., 2 months | 98.9 | 99.8 | 98.0 |
| 40° C., 4 months | 97.2 | 102.3 | 100.6 |

Example 2

To each of prescriptions 4 and 5 in Example 1 stored at 40° C. for 4 months was added 5 ml of 5% saccharide solution (aqueous glucose solution), and the stability thereof after dissolved was examined. The outward appearance, the state of the solution and the content were stable at room temperature (about 23° C.) for 8 hours.

Example 3

A lyophilized pharmaceutical preparation was prepared by mixing compound 12 obtained in Reference Example 24 with an additive (inositol) in the ratio per vial (35P) shown in Table 6. The lyophilization conditions are shown below. The sample was frozen at −50 ° C. or less for about 2 hours, and after the temperature was increased to −10° C. at a rate of 10° C./hr, the sample was subjected to primary lyophilization for 48 hours. Thereafter, the temperature was increased to 45° C. at a rate of 10° C./hr, and the sample was subjected to secondary lyophilization for 6 hours. The degree of vacuum was 0.06 Torr throughout the entire process. For returning to the atmospheric pressure, low-moisture nitrogen was used. The water content of the product as determined by the Karl Fisher method was 0.1%. In the stability test, the results in Table 7 were obtained. The stability of the composition of the present invention was improved significantly as compared with that of the Comparative Example.

TABLE 6

Stabilized Prescription for Lyophilization

|  | Prescription 6 |
| --- | --- |
| Compound 12 | 122.5 mg |
| Inositol | 50 mg |
| Injection water | 10 ml |

TABLE 7

Results of the Stability Test (Residual Compound 12 (%))

|  | Prescription 6 |
| --- | --- |
| 60° C., 2 weeks | 99.7 |
| 60° C., 1 month | 95.6 |
| 50° C., 1 month | 98.6 |

Example 4

To the prescription in Example 3 stored at 60° C. for 1 month was added 50 ml of 5% saccharide solution (aqueous glucose solution), and the stability thereof after dissolved was examined.

The outward appearance, the state of the solution and the content were stable at room temperature (about 23° C.) for 8 hours.

Example 5

A lyophilized pharmaceutical preparation was prepared by mixing compound 12 obtained in Reference Example 24 with an additive (trehalose) in the ratio per vial (35P) shown in Table 8. The lyophilization conditions were the same as in Example 3.

In the stability test, the results in Table 9 were obtained. The stability of the pharmaceutical composition of the present invention was improved significantly as compared with that of the Comparative Example.

TABLE 8

Stabilized Prescription for Lyophilization

|  | Prescription 6 |
|---|---|
| Compound 12 | 122.5 mg |
| Trehalose | 100 mg |
| Injection water | 10 ml |

TABLE 9

Result of the Stability Test (Residual Compound 12 (%))

|  | Prescription 7 |
|---|---|
| 60° C., 1 month | 99.0 |

Example 6

To the prescription in Example 5 stored at 60° C. for 1 month was added 50 ml of 5% saccharide solution (aqueous glucose solution), and the stability thereof after dissolved was examined.

The outward appearance and the state of the solution were stable at room temperature (about 23° C.) for 8 hours.

Experimental Example 1

Method: 6-week-old CDF1 female mice (n=5) were allowed to have neutropenia by intraperitoneally administering 200 mg/kg of cyclophosphamide, and after 4 days, 0.2 ml liquid of frozen and stored A. fumigatus TIMM1728 conidia, diluted 1000-fold, was inoculated into the tail veins of the mice ($6 \times 10^4$ CFU/mouse). Compound 12 was dissolved in 5% saccharide solution (aqueous glucose solution) and intravenously administered into the mice 5 times, that is, once in 2 hours after the infection and daily twice for 2 days after the infection. The number of living mice was recorded for 10 days after the infection, to evaluate the effect of prolonging their life.

Results: The defensive effect ($ED_{50}$) of Compound 12 by intravenous administration against the experimental infection of Aspergillosis in the mice was 1.7 mg/kg.

INDUSTRIAL APPLICABILITY

The composition used in the present invention is stable and particularly its lyophilized product is suitable as a pharmaceutical preparation for injection.

What is claimed is:

1. A composition comprising
a lyophilized quaternized nitrogen-containing imidazole-1-yl or 1,2,4-triazole-1-yl compound wherein one of the nitrogen atoms constituting the azole ring is quaternized with a group eliminating in vivo and represented by the formula:

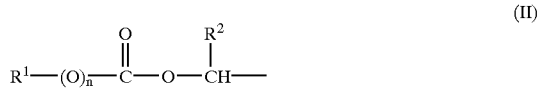

(II)

wherein
$R^1$ represents a hydrocarbon or heterocyclic group which may be substituted,
$R^2$ represents a hydrogen atom or a lower alkyl group, and
n is 0 or 1, and
a saccharide,
said compound being capable of being converted into an anti-fungal azole compound upon elimination of said group in vivo.

2. The composition according to claim 1, wherein the quaternized nitrogen-containing imidazole-1-yl or 1,2,4-triazole-1-yl compound is a compound represented by the formula:

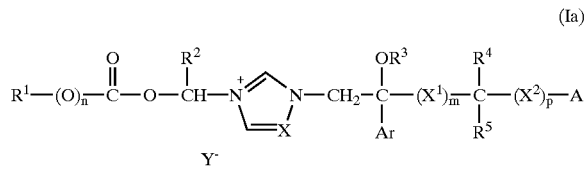

(Ia)

wherein $R^1$ represents a hydrocarbon or heterocyclic group which may be substituted, $R^2$ represents a hydrogen atom or a lower alkyl group, n is 0 or 1, X represents a nitrogen atom or a methine group, Ar represents a phenyl group which may be substituted, A represents a hydrocarbon or heterocyclic group which may be substituted, $X^1$ represents an oxygen atom or a methylene group, $X^2$ represents a sulfur atom which may be oxidized, m and p each represents 0 or 1, and $Y^-$ represents an anion, (1) $R^3$, $R^4$ and $R^5$ are the same or different and each represents a hydrogen atom or a lower alkyl group, (2) $R^3$ represents a hydrogen atom or a lower alkyl group, and $R^4$ and $R^5$ are combined to form a lower alkylene group, or (3) $R^5$ represents a hydrogen atom or a lower alkyl group, and $R^3$ and $R^4$ are combined to form a lower alkylene group.

3. The composition according to claim 1, wherein the quaternized nitrogen-containing imidazole-1-yl or 1,2,4-triazole-1-yl compound is 4-acetoxymethyl-1-[(2R, 3R)-2-(2,4-difluorophenyl)-2-hydroxy-3-[2-oxo-3-[4-(1H-tetrazol-1-yl)phenyl]-1-imidazolydinyl]butyl]-1H-1,2,4-triazolium chloride.

4. The composition according to claim 1, which is an anti-fungal agent.

5. The composition according to claim 1, wherein the saccharide is a monosaccharide, a disaccharide or sugar alcohol.

6. The composition according to claim 1, wherein the saccharide is fructose, glucose, maltose, cellobiose, gentiobiose, melibiose, lactose, turanose, sophorose, trehalose, isotrehalose, isosaccharose, white sugar, mannitol, sorbitol, xylitol or inositol.

7. The composition according to claim 1, wherein the saccharide is maltose, lactose, white sugar, mannitol, trehalose or inositol.

8. The composition according to claim 1, wherein the saccharide is inositol or trehalose.

9. The composition according to claim 1, wherein the saccharide is contained in an amount of 0.001 to 1000 parts by weight per 1 part by weight of the quaternized nitrogen-containing imidazole-1-yl or 1,2,4-triazole-1-yl compound.

10. The composition according to claim 1, wherein the saccharide is contained in an amount of 0.01 to 100 parts by weight per 1 part by weight of the quaternized nitrogen-containing imidazole-1-yl or 1,2,4-triazole-1-yl compound.

11. The composition according to claim 1, wherein the saccharide is contained in an amount of 0.1 to 10 parts by weight per 1 part by weight of the quaternized nitrogen-containing imidazole-1-yl or 1,2,4-triazole-1-yl compound.

12. The composition according to claim 1, which is a pharmaceutical preparation for injection.

13. A process for producing a lyophilized product, which comprises adding a saccharide to an aqueous solution of a quaternized nitrogen-containing imidazole-1-yl or 1,2,4-triazole-1-yl compound wherein one of the nitrogen atoms constituting the azole ring is quaternized with a group of formula:

(II)

wherein $R^1$ represents a hydrocarbon or heterocyclic group which may be substituted, $R^2$ represents a hydrogen atom or a lower alkyl group, and n is 0 or 1, eliminating in vivo, and then lyophilizing the mixture, said compound being capable of being converted into an anti-fungal azole compound upon elimination of said group in vivo.

14. A method of stabilizing a quaternized nitrogen-containing imidazole-1-yl or 1,2,4-triazole-1-yl compound in a lyophilized product, which comprises adding a saccharide to an aqueous solution of a quaternized nitrogen-containing imidazole-1-yl or 1,2,4-triazole-1-yl compound wherein one of the nitrogen atoms constituting the azole ring is quaternized with a group of formula:

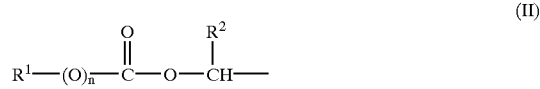

(II)

wherein $R^1$ represents a hydrocarbon or heterocyclic group which may be substituted, $R^2$ represents a hydrogen atom or a lower alkyl group, and n is 0 or 1, eliminating in vivo, and then lyophilizing the mixture, said compound being capable of being converted into an anti-fungal azole compound upon elimination of said group in vivo.

15. A method of making a pharmaceutical preparation for injection comprising mixing a lyophilized quaternized nitrogen-containing imidazole-1-yl or 1,2,4-triazole-1-yl compound wherein one of the nitrogen atoms constituting the azole ring is quaternized with a group eliminating in vivo and represented by the formula:

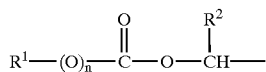

(II)

wherein
$R^1$ represents a hydrocarbon or heterocyclic group which may be substituted,
$R^2$ represents a hydrogen atom or a lower alkyl group, and
n is 0 or 1,
and a saccharide,
said compound being capable of being converted into an anti-fungal azole compound upon elimination of said group in vivo.

* * * * *